(12) United States Patent  
Yorkston et al.

(10) Patent No.: US 8,210,745 B2  
(45) Date of Patent: Jul. 3, 2012

(54) EXTREMITY IMAGING APPARATUS FOR CONE BEAM COMPUTED TOMOGRAPHY

(76) Inventors: John Yorkston, Penfield, NY (US);
William F. Snyder, Hilton, NY (US);
Jeffrey H. Siewerdsen, Baltimore, MD (US)

( * ) Notice: Subject to any disclaimer, the term of this patent is extended or adjusted under 35 U.S.C. 154(b) by 0 days.

(21) Appl. No.: 13/076,705

(22) Filed: Mar. 31, 2011

(65) Prior Publication Data

US 2011/0228901 A1    Sep. 22, 2011

Related U.S. Application Data

(63) Continuation-in-part of application No. 12/771,250, filed on Apr. 30, 2010.

(60) Provisional application No. 61/322,516, filed on Apr. 9, 2010, provisional application No. 61/422,679, filed on Dec. 14, 2010, provisional application No. 61/175,091, filed on May 4, 2009.

(51) Int. Cl.
*H05G 1/04* (2006.01)

(52) U.S. Cl. ............................................. 378/196; 378/4

(58) Field of Classification Search ................ 378/4, 11, 378/13, 14, 19, 195, 196, 197
See application file for complete search history.

(56) References Cited

U.S. PATENT DOCUMENTS

| | | | |
|---|---|---|---|
| 4,316,091 A | 2/1982 | Bernardi | |
| 5,014,293 A * | 5/1991 | Boyd et al. | ..... 378/197 |
| 5,748,704 A | 5/1998 | Mazess et al. | |
| 6,236,704 B1 | 5/2001 | Navab et al. | |
| 6,940,941 B2 | 9/2005 | Gregerson et al. | |
| 7,001,045 B2 | 2/2006 | Gregerson et al. | |
| 7,224,764 B2 | 5/2007 | Sukovic et al. | |
| 7,388,941 B2 | 6/2008 | Sukovic et al. | |
| 7,394,888 B2 * | 7/2008 | Sukovic et al. | ..... 378/20 |
| 2004/0022350 A1 * | 2/2004 | Gregerson et al. | ..... 378/15 |
| 2008/0101533 A1 | 5/2008 | Ein-Gal | |
| 2008/0205584 A1 | 8/2008 | Sukovic et al. | |

FOREIGN PATENT DOCUMENTS

DE    10146915    4/2003

OTHER PUBLICATIONS

PCT Search Report, dated Nov. 22, 2010, International Appl. No. PCT/US2010/001308, 4 pages.
Page from website = www.planmed.com, 1 page, Mar. 2011.
International Search Report, dated Nov. 22, 2011, International Appl. No. PCT/US2011/000596, 2 pages.

* cited by examiner

*Primary Examiner* — Hoon Song

(57) ABSTRACT

An apparatus for cone beam computed tomography of lower leg portions of a patient has a radiation source and a source transport actuable to move the source along an arcuate source path within a housing, from one side of a circumferential gap to the other and has a radius R2 about a center. A housing is provided for placement of the patient's foot. A digital radiation detector has a detector transport actuable to move the detector along an arcuate detector path within the housing, the detector path having a radius R1 about the center and concentric with the source path, wherein R1 is less than R2, and wherein the detector path extends from one side of the pedestal indent to the other. A gap closure apparatus is movable to a position that continues the detector path across the circumferential gap and encloses the detector path.

15 Claims, 40 Drawing Sheets

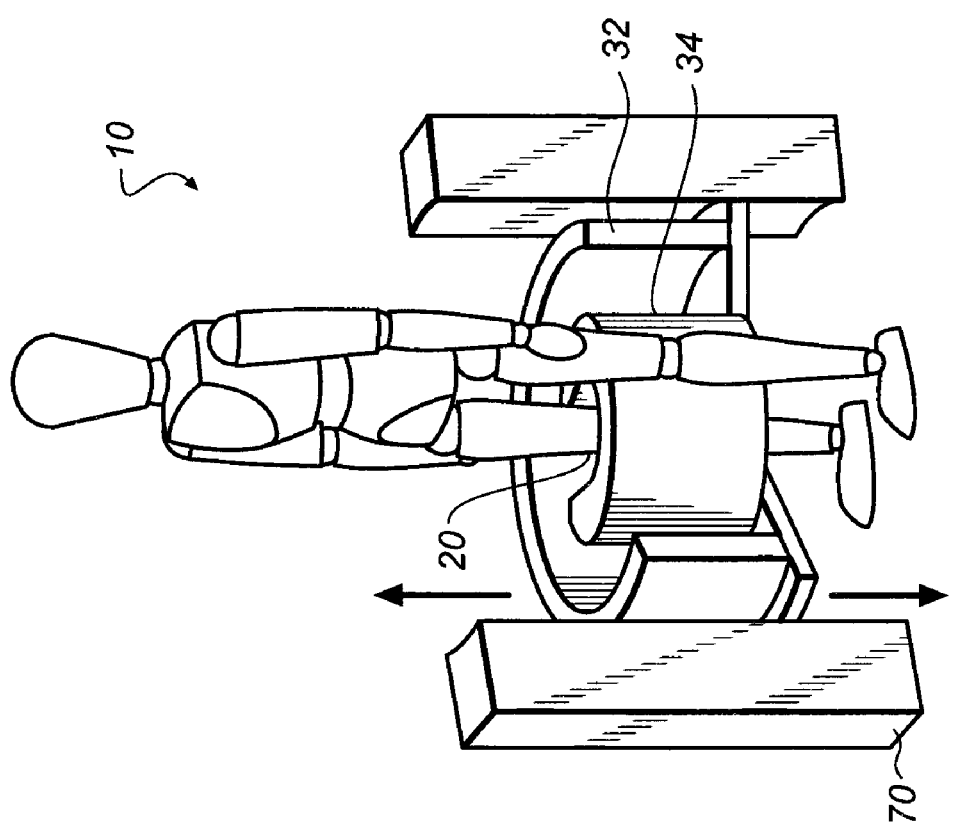

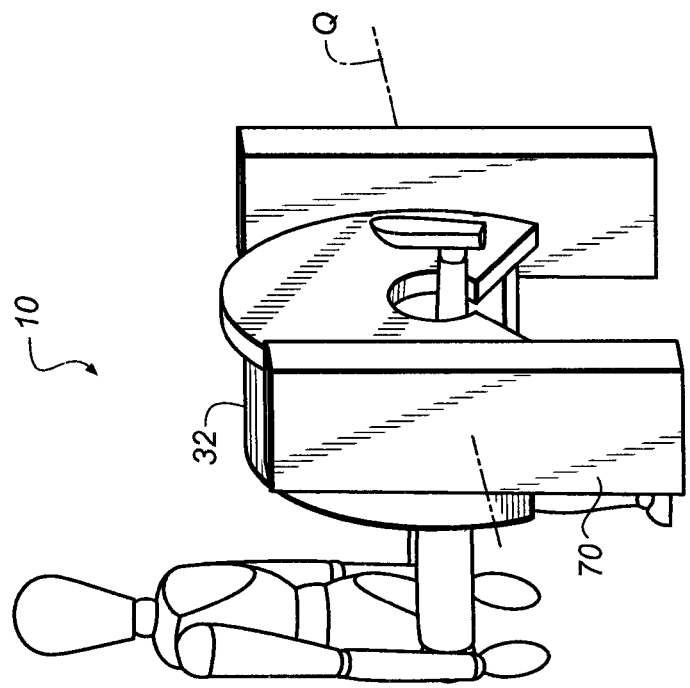
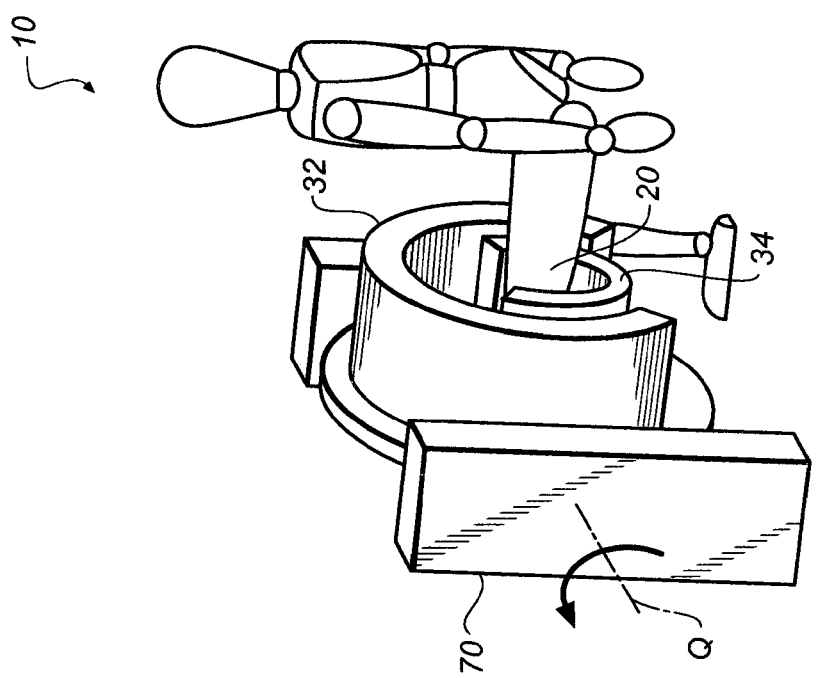
FIG. 8B
FIG. 8A

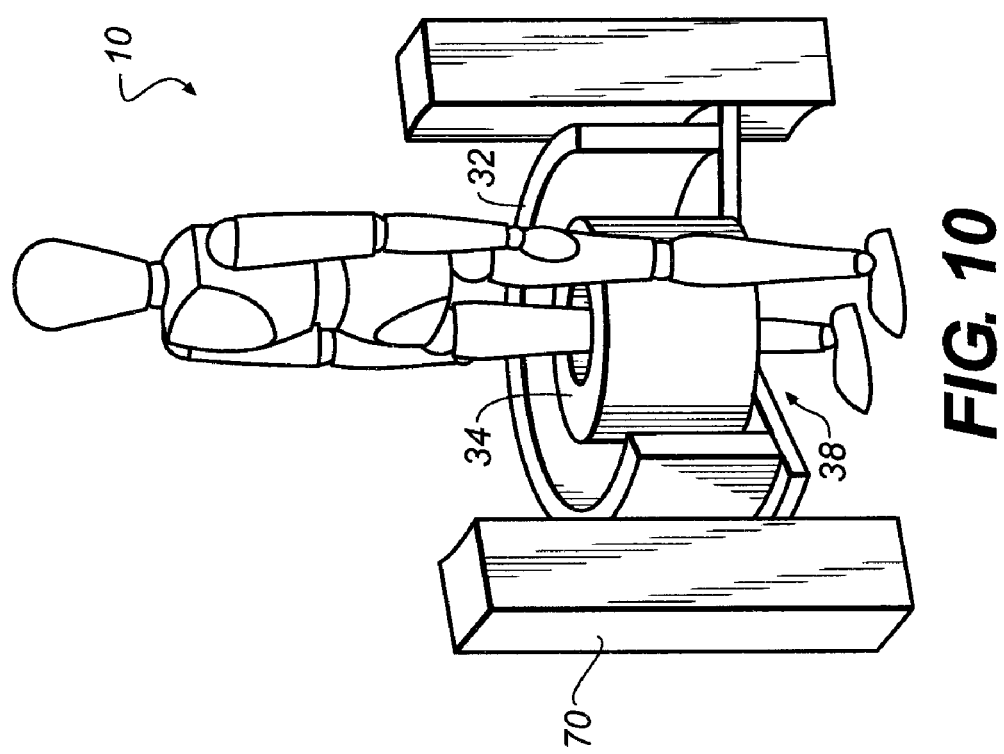

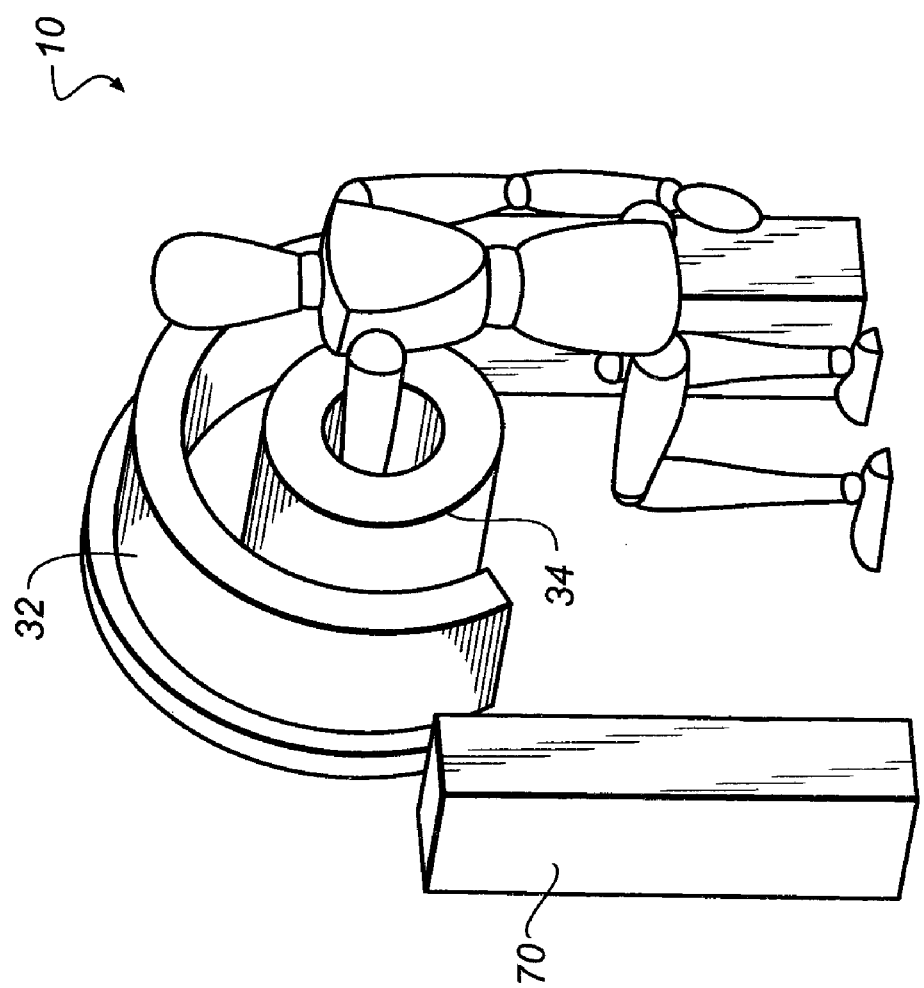

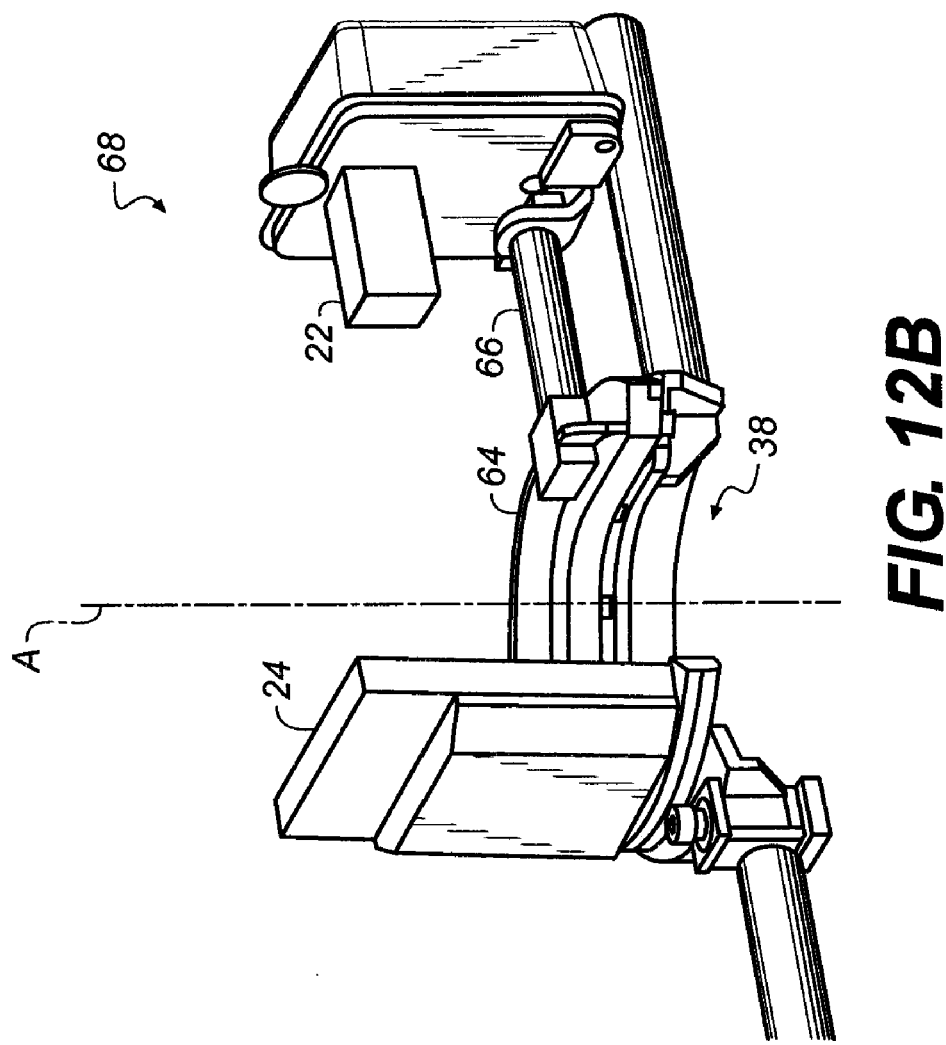

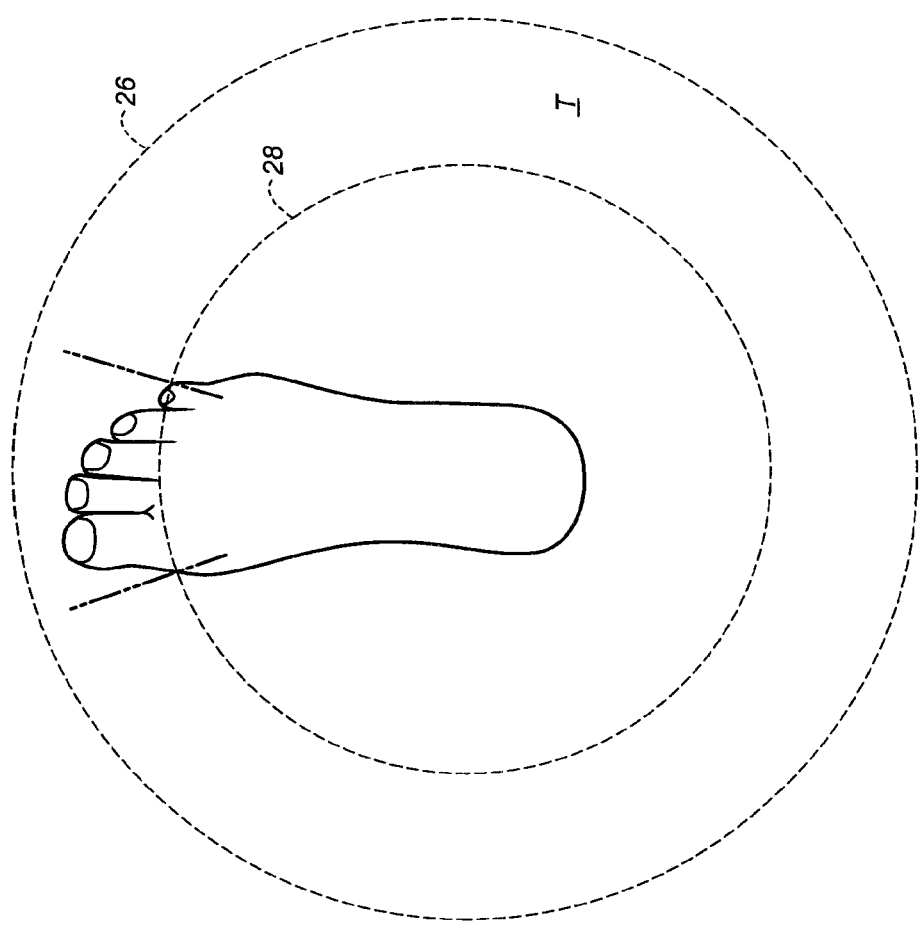

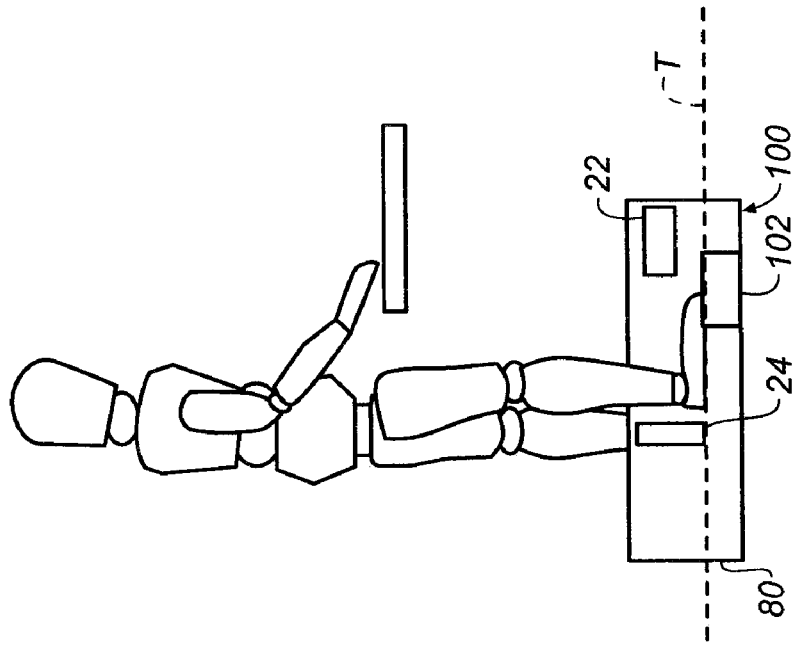
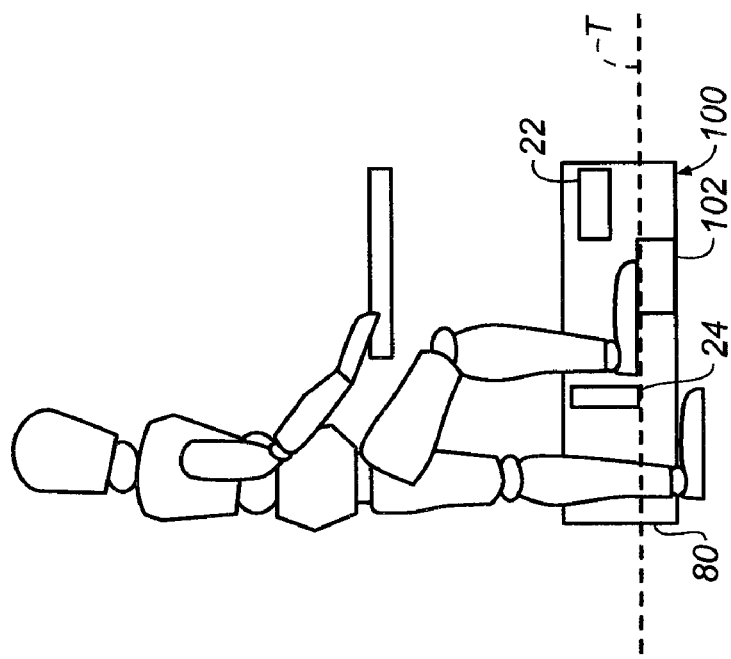

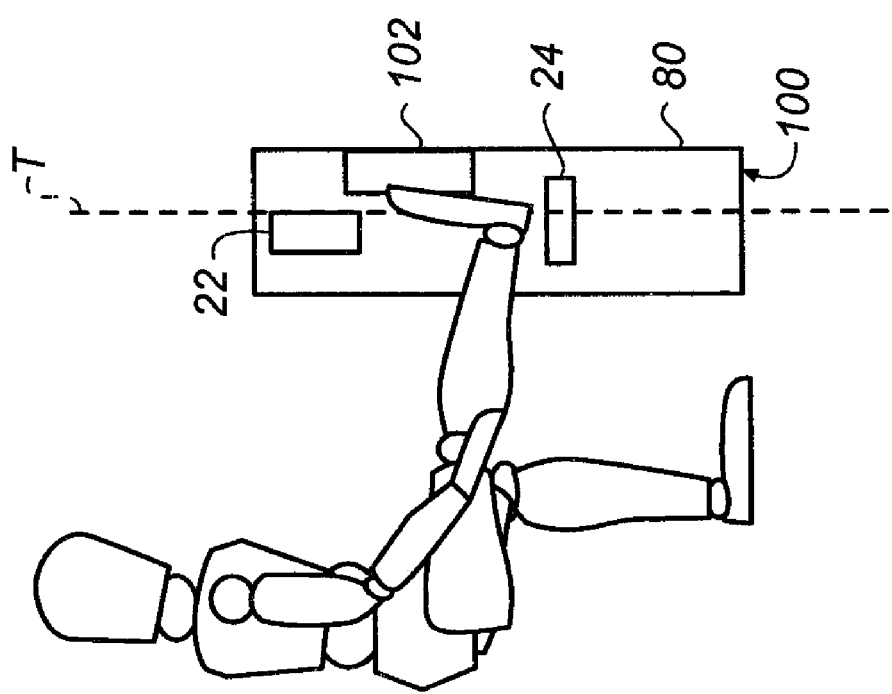

EXTREMITY IMAGING APPARATUS FOR CONE BEAM COMPUTED TOMOGRAPHY

CROSS REFERENCE TO RELATED APPLICATIONS

This application claims priority to U.S. Ser. No. 61/322,516, provisionally filed on Apr. 9, 2010, entitled "Cone Beam CT Apparatus for Medical Imaging", to Yorkston et al.

This application claims priority to U.S. Ser. No. 61/422,679, provisionally filed on Dec. 14, 2010, entitled "EXTREMITY IMAGING APPARATUS FOR CONE BEAM COMPUTED TOMOGRAPHY", to Yorkston et al.

This is a Continuation-in-Part of U.S. Ser. No. 12/771,250, filed on Apr. 30, 2010, entitled "EXTREMITY IMAGING APPARATUS FOR CONE BEAM COMPUTED TOMOGRAPHY" to Yorkston et al., which claims priority to U.S. Serial No. 61/175,091 provisionally filed on May 4, 2009, entitled "Cone Beam Computed Tomography (CBCT) For Extremity Imaging".

These references are incorporated herein by reference.

FIELD OF THE INVENTION

The invention relates generally to diagnostic imaging and in particular to cone beam imaging systems used for obtaining volume images of extremities.

BACKGROUND OF THE INVENTION

3-D volume imaging has been employed as a diagnostic tool that offers advantages over earlier 2-D radiographic imaging techniques for evaluating the condition of internal structures and organs. 3-D imaging of a patient or other subject has been made possible by a number of advancements, including the development of high-speed imaging detectors, such as digital radiography (DR) detectors that enable multiple images to be taken in rapid succession.

Cone beam computed tomography (CBCT) or cone beam CT technology offers promise as one type of diagnostic tool for providing 3-D volume images. Cone beam CT systems capture volumetric data sets by using a high frame rate digital radiography (DR) detector and an x-ray source, typically affixed to a gantry that rotates about the object to be imaged, directing, from various points along its orbit around the subject, a divergent cone beam of x-rays toward the subject. The CBCT system captures projections throughout the rotation, for example, one 2-D projection image at every degree of rotation. The projections are then reconstructed into a 3D volume image using various techniques. Among the most common methods for reconstructing the 3-D volume image are filtered back projection approaches.

Although 3-D images of diagnostic quality can be generated using CBCT systems and technology, a number of technical challenges remain. In some cases, for example, there can be a limited range of angular rotation of the x-ray source and detector with respect to the subject. CBCT Imaging of legs, arms, and other extremities can be hampered by physical obstruction from a paired extremity. This is an obstacle that is encountered in obtaining CBCT image projections for the human leg or knee, for example. Not all imaging positions around the knee are accessible; the patient's own anatomy prevents the radiation source and image detector from being positioned over a portion of the scan circumference.

To illustrate the problem faced in CBCT imaging of the knee, the top view of FIG. 1 shows the circular scan paths for a radiation source 22 and detector 24 when imaging the right knee R of a patient as a subject 20. Various positions of radiation source 22 and detector are shown in dashed line form. Source 22, placed at some distance from the knee, can be positioned at different points over an arc of about 200 degrees; with any larger arc, left knee L blocks the way. Detector 24, smaller than source 22 and typically placed very near subject 20, can be positioned between the patient's right and left knees and is thus capable of positioning over the full circular orbit.

A full 360 degree orbit of the source and detector is not needed for conventional CBCT imaging; instead, sufficient information for image reconstruction can be obtained with an orbital scan range that just exceeds 180 degrees by the angle of the cone beam itself, for example. However, in some cases it can be difficult to obtain much more than about 180 degree revolution for imaging the knee or other joints and other applications. Moreover, there can be diagnostic situations in which obtaining projection images over a certain range of angles has advantages, but patient anatomy blocks the source, detector, or both from imaging over that range.

For imaging the leg, one way around this problem is to arrange the patient in a pose such that the subject leg is extended into a CBCT scanning apparatus and the paired leg is supported in some other way or bent with respect to the subject leg, such as at a right angle. This is the approach used, for example, in the CT scanner device taught in U.S. Pat. No. 7,394,888 entitled "CT Scanner for Lower Extremities" to Sukovic et al. In the methods of the Sukovic et al. '888 disclosure, the other leg must either be lifted out of place or spread at a distance, or is relaxed while the subject leg is lifted out of place and extended into the scanner equipment. This arrangement can be particularly disadvantageous for a number of reasons. It can be helpful, for example, to examine the condition of a knee or ankle joint under the normal weight load exerted on that joint by the patient. But, in requiring the patient to assume a position that is not usually encountered in typical movement, the Sukovic et al. '888 apparatus may obtain an image when there is excessive strain, or insufficient strain, or poorly directed strain, on the joint.

Another problem with conventional approaches relates to imaging of a load-bearing extremity such as the human leg. Because of the inability to image the leg under a normal load, as the patient is in a standing position, various artificial ways of mimicking load conditions have been attempted. Such approaches have used various types of braces, compression devices, and supports. As one example intended to remedy the shortcomings of conventional imaging techniques, the Sukovic et al. '888 disclosure teaches simulating the normal loading of the leg by elevating the leg to a non-standing position, then applying an external force against the leg. However, it can be readily appreciated that while this type of simulation allows some approximation of load-bearing limb response, it can be inaccurate. The knee or ankle joint, under some artificially applied load and at an angle not taken when standing, may not behave exactly as it does when bearing the patient's weight in a standing position.

Another difficulty with the Sukovic et al. '888 apparatus and with other devices designed to address knee, lower leg, and foot imaging relates to poor image quality. For image quality, the CBCT sequence requires that the detector be up close to the subject and the source of the cone beam radiation be at a sufficient distance from the subject. This provides the best image and reduces image truncation and consequent lost data. Positioning the subject midway between the detector and the source, as Sukovic et al. '888 apparatus and with other devices require, not only noticeably compromises image quality, but also places the patient too near the radiation source, so that radiation levels are considerably higher.

One example of this strategy is shown in German patent publication DE 10146915. With the C-shaped gantry arrangement shown, centering the subject at the center of rotation of source and detector would apply considerably higher radiation amounts with each projection and severely compromise image quality. Any other positioning of the subject, such as closer to the detector, might reduce radiation levels over some part of the image capture sequence, but would result in unduly complex image reconstruction problems, since this would actually vary the distances between radiation source and subject and between subject and detector with each projection image obtained. Attempted imaging of the knee with such a system would require the patient to be supported in some way, balancing on the leg being imaged. It can be appreciated that this requirement is unreasonable or impossible for many situations in which an injured knee is being imaged. Thus, the C-shaped gantry shown would not be suitable for imaging only one knee of the patient. The solution described would irradiate both knees, increasing the amount of tissue exposed to radiation and reducing image quality.

Imaging of the foot and ankle presents additional obstacles for CBCT projection image capture. The shape of the foot itself makes it difficult to provide a suitable path for the x-ray source and detector for obtaining a set of projection images that can be used for accurate 3-D reconstruction. Approaches such as that given in the Sukovic et al. '888 disclosure, centering the foot between source and detector, suffer from the same problems of poorly positioned exposure and noticeably compromised image quality.

A number of conventional imaging approaches for the lower leg function by imaging both legs at the same time. This type of conventional solution suffers from reduced image quality and increases the amount of patient anatomy that receives radiation.

It can be seen that although a number of solutions have been proposed to address the problem of CBCT extremity imaging, conventional solutions fall short of what is needed with regard to both usability and performance.

SUMMARY OF THE INVENTION

It is an object of the present invention to advance the art of diagnostic imaging of extremity body parts, particularly jointed or load-bearing, paired extremities such as knees, legs, ankles, fingers, hands, wrists, elbows, arms, and shoulders.

It is a feature of the present invention that it provides an apparatus with different radii for orbital paths of sensor and radiation source components.

It is an advantage of the present invention that it allows imaging of foot and ankle extremities for a patient who is standing or sitting.

According to one aspect of the present invention there is provided an apparatus for cone beam computed tomography of a portion of a lower leg of a patient, the apparatus comprising: a radiation source; a radiation source transport actuable to move the source along at least a portion of an arcuate source path within a housing, wherein the source path extends from one side of a circumferential gap in the housing to the other side of the circumferential gap and has a radius R2 about a center; a pedestal indent on the housing for placement of the patient's foot; a digital radiation detector; a detector transport actuable to move the detector along at least a portion of an arcuate detector path within the housing, the detector path having a radius R1 about the center and concentric with the source path, wherein R1 is less than R2, and wherein the detector path extends from one side of the pedestal indent to the other; and a gap closure apparatus that is movable to a position that continues the detector path across the circumferential gap and that encloses the detector path.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 7 is a perspective view showing optional height adjustment.

FIGS. 8A and 8B are perspective views that show extremity imaging for an extended leg in an alternate configuration.

FIG. 10 is a perspective view that shows imaging with the detector transport fully encircling the lower extremity.

FIG. 11 is a perspective view that shows imaging with the detector transport fully encircling the upper extremity.

FIG. 12B is a perspective view of an imaging apparatus using a turntable for source and detector transport.

FIG. 18B is a schematic view showing the shape of the foot relative to source and detector paths.

FIG. 19A is a schematic view showing patient positioning for CBCT imaging of the foot in a non-load-bearing position.

FIG. 19B is a schematic view showing patient positioning for CBCT imaging of the foot in a load-bearing position.

FIG. 19C is a schematic view showing patient positioning for CBCT imaging of the foot in a non-load-bearing position with the patient seated and the leg extended.

DETAILED DESCRIPTION OF THE INVENTION

Figure 1:
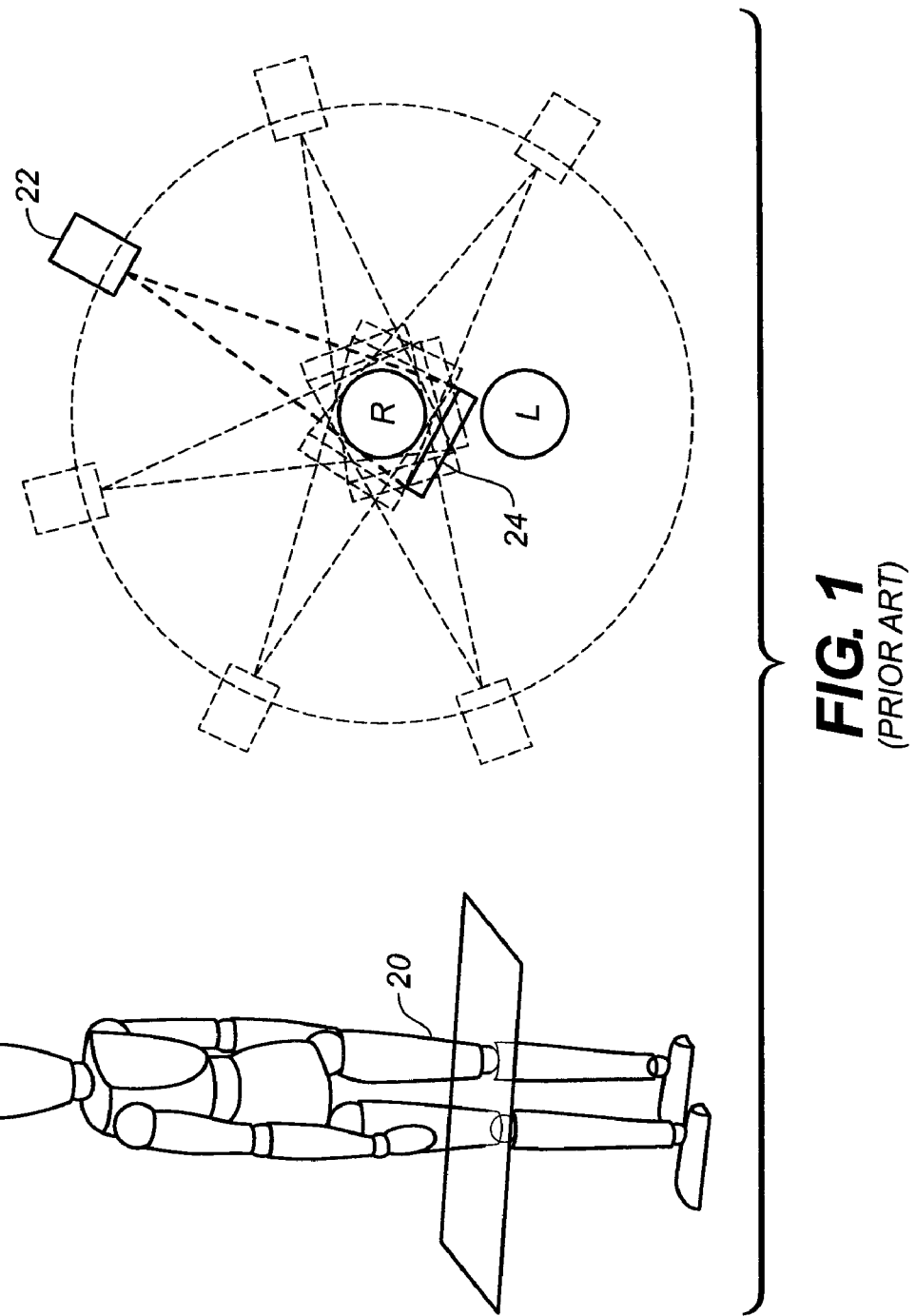
FIG. 1 is a schematic view showing the geometry and limitations of CBCT scanning for portions of the lower leg.

The following is a detailed description of the preferred embodiments of the invention, reference being made to the drawings in which the same reference numerals identify the same elements of structure in each of the several figures.

In extremity imaging, particularly for imaging the lower paired extremities, improvements are needed, including the following:

(i) improved placement of the radiation source and detector to provide acceptable radiation levels and image quality throughout the scanning sequence;

(ii) system flexibility for imaging at different heights with respect to the rotational axis of the source and detector, including the flexibility to allow imaging with the patient standing or seated comfortably, such as with a foot in an elevated position, for example;

(iii) improved patient accessibility, so that the patient does not need to contort, twist, or unduly stress limbs or joints that may have been injured in order to provide images of those body parts;

(iv) improved ergonomics for obtaining the CBCT image, allowing the patient to stand with normal posture, for example. This would also allow load-bearing extremities, such as legs, knees, and ankles, to be imaged under the normal load exerted by the patient's weight, rather than under simulated loading conditions as taught in the Sukovic et al. '888 disclosure and elsewhere;

(v) capability for CBCT imaging of the foot or ankle. The inherent difficulty that is due to the shape of the foot is one factor; other problems with foot imaging include the need to be able to image the foot in a number of different positions, with and without weight-bearing.

In the context of the present disclosure, the term "extremity" has its meaning as conventionally understood in diagnostic imaging parlance, referring to knees, legs, ankles, fingers, hands, wrists, elbows, arms, and shoulders and any other anatomical extremity. The term "subject" is used to describe the extremity of the patient that is imaged, such as the "subject leg", for example. The term "paired extremity" is used in general to refer to any anatomical extremity wherein normally two or more are present on the same patient. In the context of the present invention, the paired extremity is not imaged; only the subject extremity is imaged.

To describe the present invention in detail, the examples given herein for embodiments of the present invention focus on imaging of the load-bearing lower extremities of the human anatomy, such as the leg, the knee, the ankle, and the foot, for example. However, these examples are considered to be illustrative and non-limiting.

In the context of the present disclosure, the term "arc" or, alternately, "circular arc", has its conventional meaning as being a portion of a circle of less than 360 degrees or, considered alternately, of less than $2\pi$ radians for a given radius.

Embodiments of the present invention address the difficulties of lower extremity imaging by providing an imaging apparatus that defines orbital source and detector paths, concentric about a center point, wherein components that provide the source and detector paths are configured to allow patient access prior to and following imaging and configured to allow the patient to stand with normal posture during the CBCT image capture series. In embodiments of the present invention, this capability is effected by using a detector transport device that has a circumferential access opening allowing positioning of the extremity, wherein the detector transport device is revolved about the positioned extremity once it is in place, enclosing the extremity as it is revolved through at least a portion of the scan.

It is instructive to consider dimensional attributes of the human frame that can be considerations for design of CBCT equipment for scanning extremities. For example, an adult human patient of average height in a comfortable standing position has left and right knees generally anywhere from about 10 to about 35 cm apart. For an adult of average height, exceeding about 35-40 cm (14-15.7 inches) between the knees becomes increasing less comfortable and out of the range of normal standing posture. It is instructive to note that this constraint makes it impractical to use gantry solutions such as that shown in DE 10146915, described earlier, for knee imaging. Either the source or the detector must be able to pass between the legs of a standing patient for single-knee CBCT imaging, a capability not available with gantry or other conventional solutions.

Figure 2:
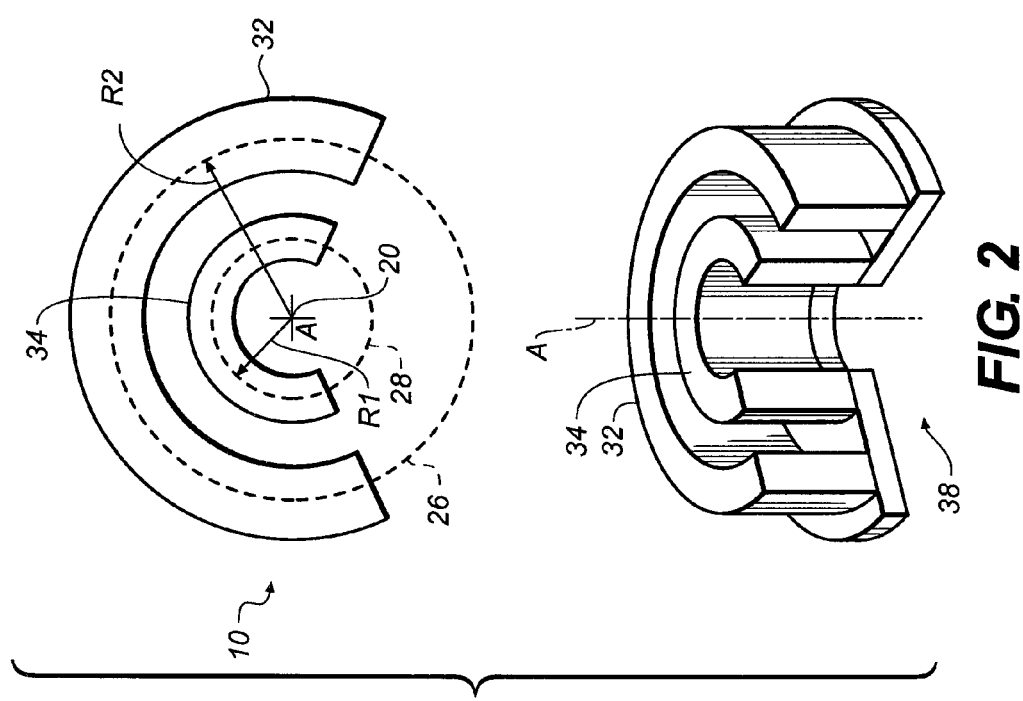
FIG. 2 shows a top and perspective view of the scanning pattern for an imaging apparatus according to an embodiment of the present invention.

The perspective and top views of FIG. 2 show how the scanning pattern is provided using various embodiments of a CBCT imaging apparatus 10 according to the present invention. A detector path 28 of a suitable radius R1 from a central axis A is provided by a first device, a detector transport 34. A source path 26 of a second, larger radius R2 is provided by a second device, a source transport 32. The extremity, subject 20, is substantially centered along central axis A so that central axis A can be considered as a line through points in subject 20. The limiting geometry for image capture is due to the arc of source transport 32, blocked by patient anatomy, such as by a paired limb, to typically about 200 degrees, as noted previously. Another limitation relates to the desirable goal of not exposing the patient more than necessary. This defines a partial circular sector, bounded by this arc and radii at start and end-of-scan.

Figure 3:
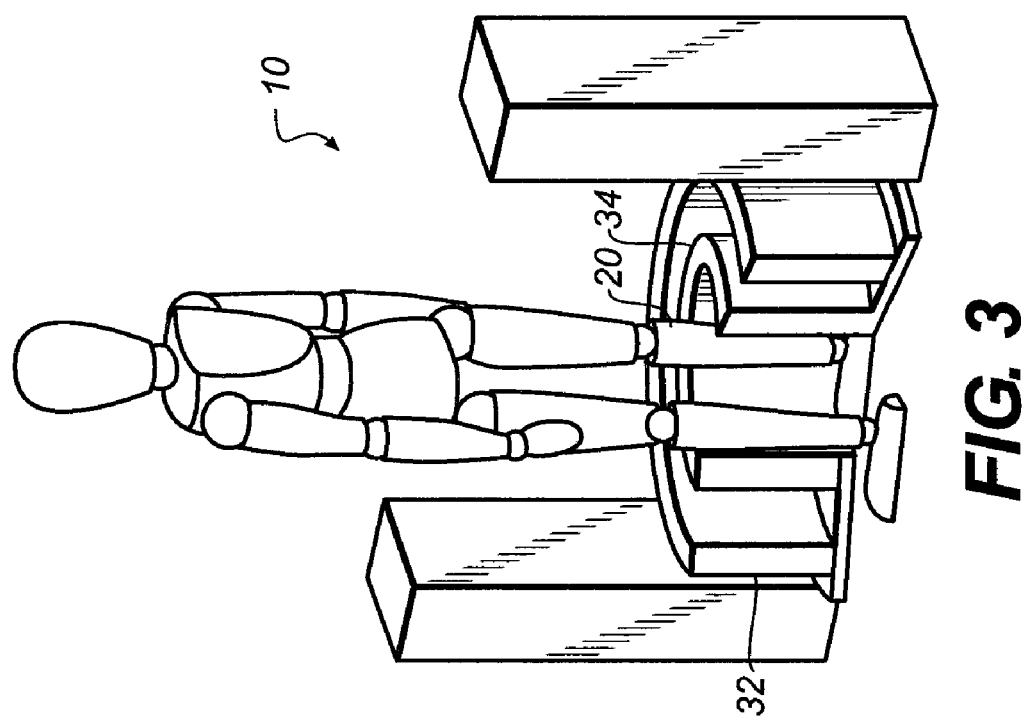
FIG. 3 is a perspective view showing patient access to an imaging apparatus with the access door open according to an embodiment of the present invention.
Figure 4:
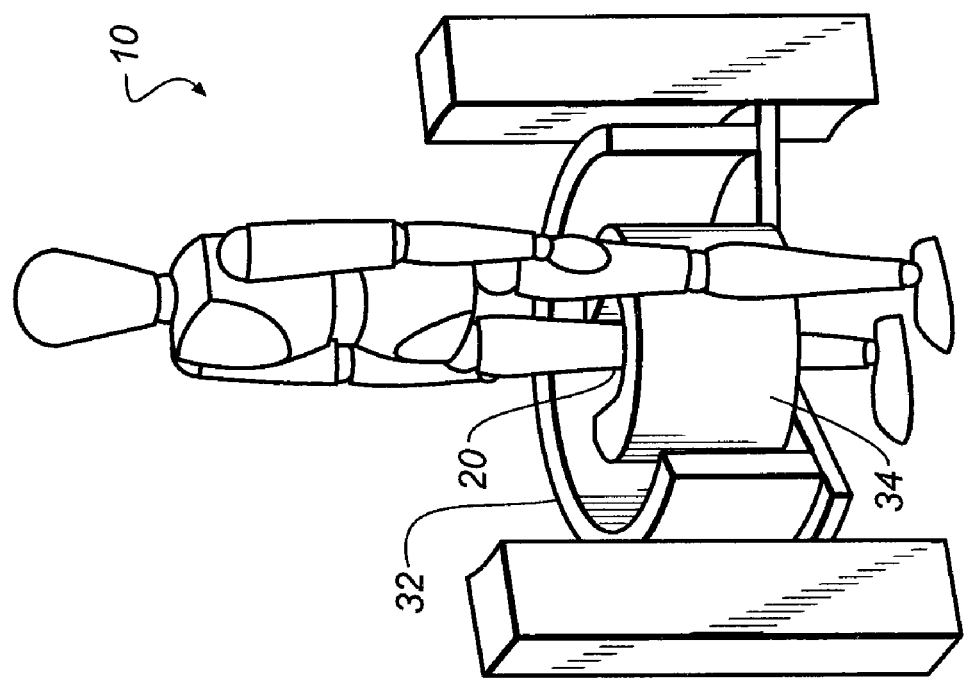
FIG. 4 is a perspective view showing the patient in a scanning position with the access door closed.

Detector transport 34, while capable of a fully circular orbit because it can be moved between the standing patient's legs, follows the necessary complementary arc to that of source transport 32. Patient access before scanning is eased by providing a circumferential gap 38 in detector transport 34. With detector transport 34 in the open position shown in FIG. 3, the patient can freely move in and out of position for imaging. When the patient is properly in position, detector transport 34 is revolved about axis A, substantially 180 degrees. This orbital movement confines the extremity more narrowly and places detector 24, not visible in FIGS. 2-4 due to the detector transport 34 housing, in position near subject 20 for obtaining the first projection image in sequence.

Circumferential gap 38 not only allows access for positioning of the subject leg or other extremity, but also allows sufficient space for the patient to stand in normal posture during imaging, placing the subject leg for imaging in the central position of axis A (FIG. 2) and the non-imaged paired leg within the space defined by circumferential gap 38. Circumferential gap 38 extends approximately 360 degrees minus the sum of 180 degrees plus the fan angle, which is determined by source-detector geometry and distance.

Figure 5:
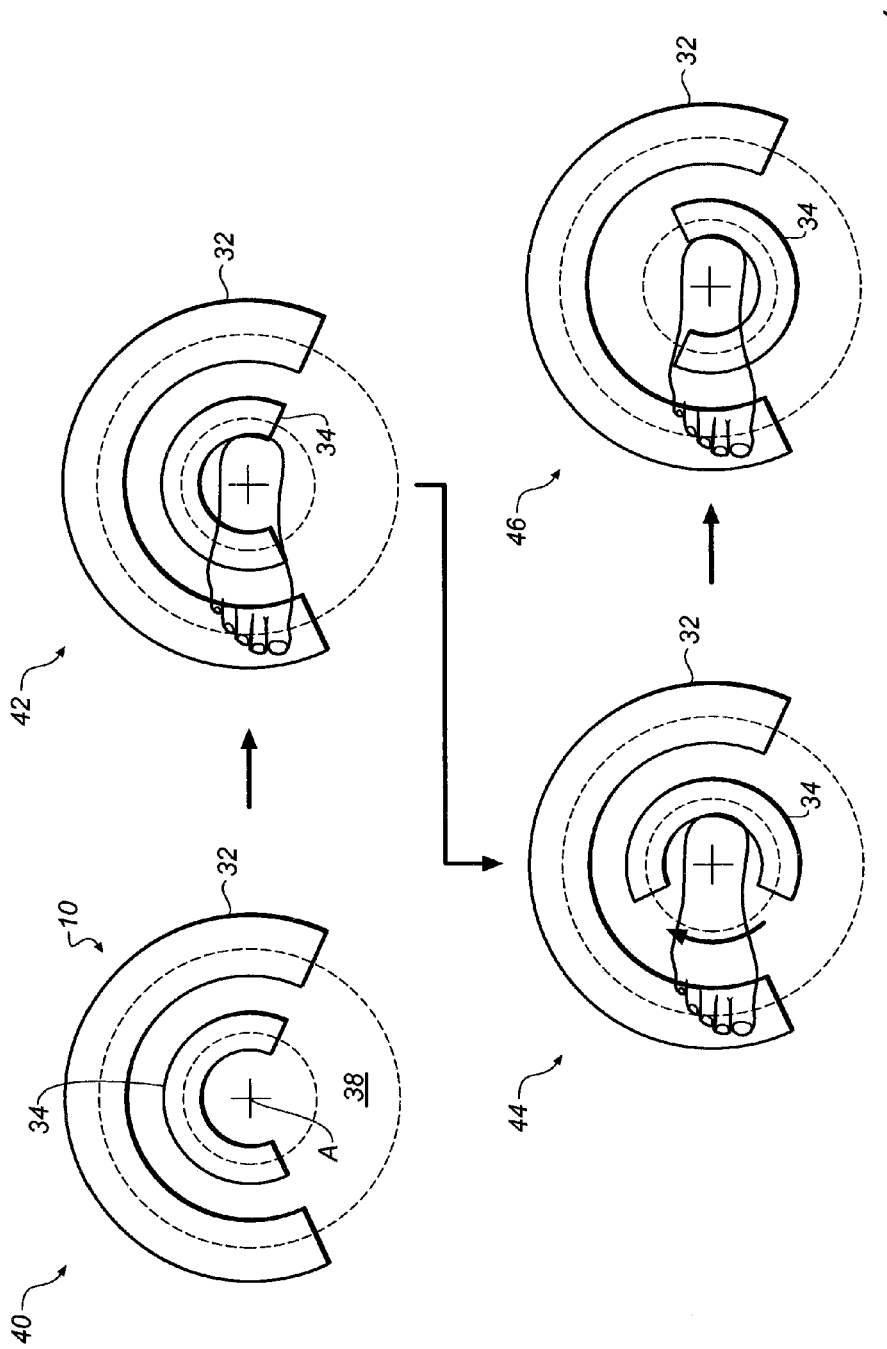
FIG. 5 is a series of top schematic views showing the sequence for patient access and system preparation for CBCT imaging.

The top views of FIG. 5 show the sequence for patient access for imaging apparatus 10. In an open access position 40, circumferential gap 38 permits access of the extremity so that it can be centered in position along central axis A. The outline of the foot corresponding to an open access position 42 indicates positioning of the patient and is shown for reference. In this example, the left leg is the subject imaged; the paired right leg would lie within or just outside circumferential gap 38. Once the patient's leg or other extremity is in place, detector transport 34, or a hooded cover or other member that defines this transport path, can be revolved into position, closing the detector portion of circumferential gap 38, as shown in a revolving transport position 44. A transport in place position 46 shows detector transport 34 in suitable position for executing the CBCT imaging sequence.

Figure 6:
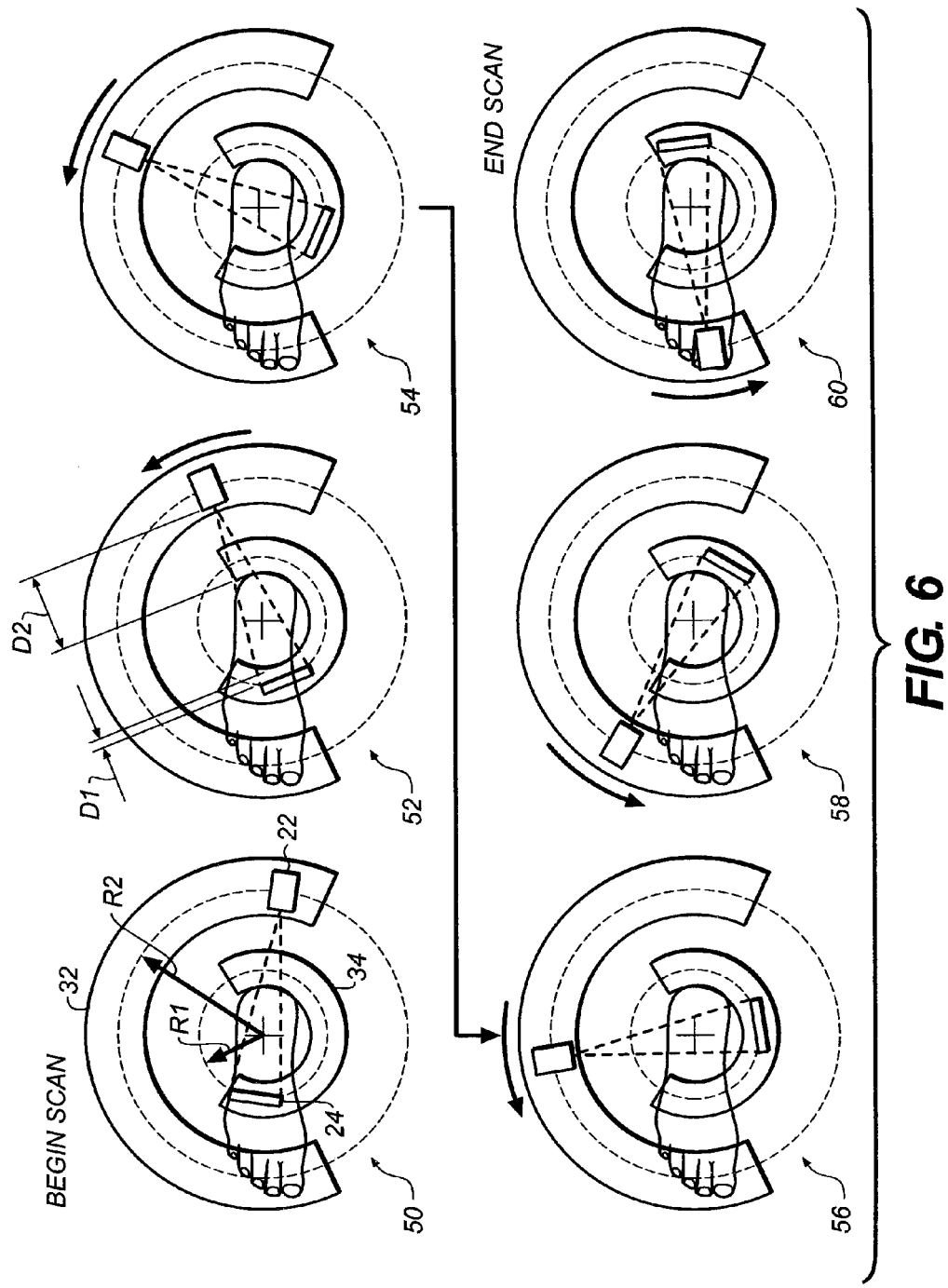
FIG. 6 is a series of top schematic views showing the sequence for obtaining CBCT projections at a number of angular positions.

The top views of FIG. 6 continue the operational sequence begun in FIG. 5 and show the sequence for obtaining CBCT projections at a number of angular positions when using imaging apparatus 10. The relative positions of radiation source 22 and detector 24, which may be concealed under a hood, as noted earlier, are shown in FIG. 6. The outline of the foot is a reference for indicating the relative position of the patient's leg; imaging of the foot itself is shown and described in more detail subsequently. The source and detector are diametrically opposite at each position during the CBCT scan and projection imaging. The sequence begins at a begin scan position 50, with radiation source 22 and detector 24 at initial positions to obtain an image at a first angle. Then, both radiation source 22 and detector 24 revolve about axis A as represented in interim scan positions 52, 54, 56, and 58. Imaging terminates at an end scan position 60. As this sequence shows, source 22 and detector 24 are in diametrically opposing positions relative to subject 20 at each imaging angle. Throughout the scanning cycle, detector 24 is within a short distance D1 of subject 20. Source 22 is positioned beyond a longer distance D2 of subject 20. The positioning of source and detector components can be carried out by separate actuators, one for each transport path, or by a single rotatable member, as described in more detail subsequently. It should be noted that scanning motion in the opposite direction, that is, clockwise with respect to the example shown in FIG. 6, is also possible, with the corresponding changes in initial and terminal scan positions.

Other features of imaging apparatus 10 are provided by the capability to move both source and detector transports 32 and 34 along the axis direction as a unit, as shown in the perspective view of FIG. 7. A vertical support 70 provides vertical transport of the imaging apparatus, so that the source and detector can be translated upwards or downwards in the direction of the central axis in order to suit patients of different heights and to image different portions of the leg. The height adjustment can be made before or after the patient's subject leg to be imaged is enclosed by detector transport 34 using the setup sequence of FIG. 5.

Figure 9:
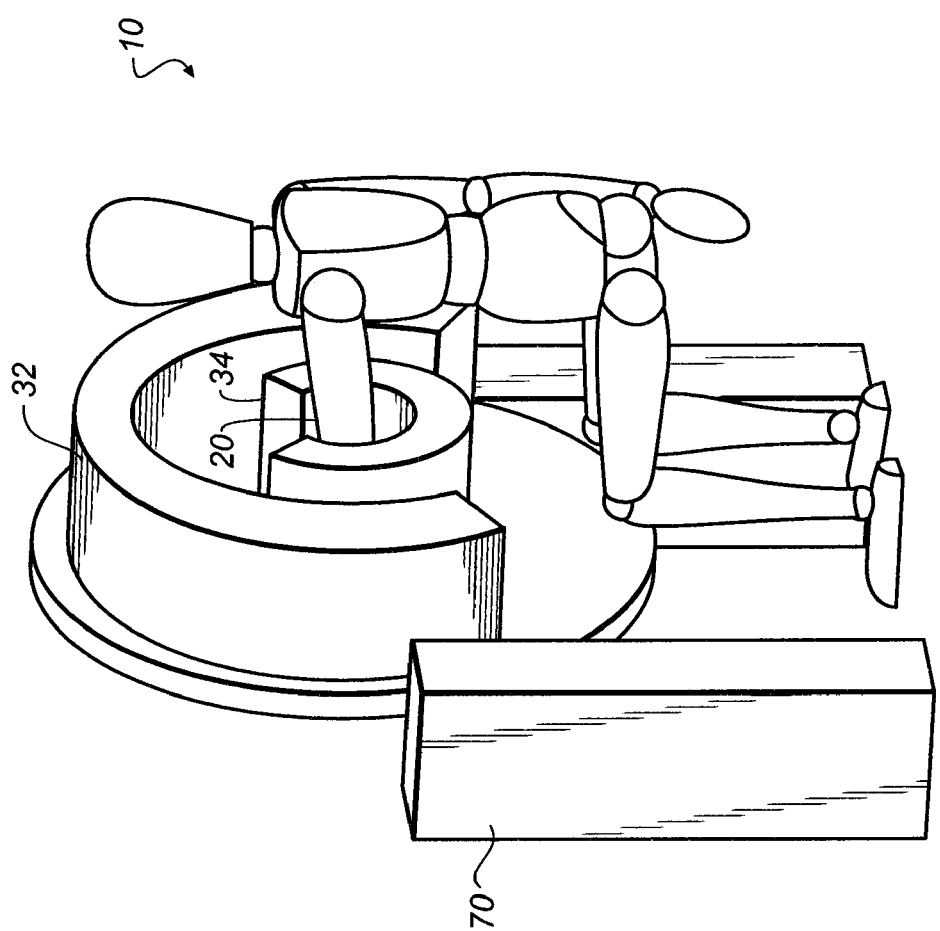
FIG. 9 is a perspective view that shows a configuration of the imaging apparatus for upper extremity imaging.

In one embodiment, vertical support 70 also allows rotation of the CBCT imaging apparatus 10 to allow imaging of an extremity that is disposed horizontally or is extended at some oblique angle other than vertical. FIGS. 8A and 8B show perspective views of knee imaging in a horizontal position, with the patient seated and the leg outwardly extended. Full 360 degree rotation about a tilt axis Q is possible. It should be noted that, with this application, similar patient accessibility applies, with detector transport 34 revolved into position once the extremity is centered in place. Further height adjustment is also possible, such as for arm, elbow, or shoulder imaging, as shown in FIG. 9.

Using revolving detector transport 34 simplifies patient access and provides sufficient imaging path for CBCT imaging, since the angular limitation of the orbital imaging path is due to source obstruction, rather than to the detector path. Thus, for example, detector transport 34 could fully encircle the limb, as shown in the examples of FIGS. 10 and 11. In these embodiments, there is a circumferential gap 38 only in the source orbit.

Referring back to the schematic diagrams of FIG. 6, radiation source 22 and detector 24 each orbit the subject along an arc with radii R2 and R1, respectively. Within source transport 32, a source actuator could be used, cooperating with a separate, complementary detector actuator that is part of detector transport 34. Thus, two independent actuator devices, one in each transport assembly, can be separately controlled and coordinated by an external logic controller to move source 22 and detector 24 along their respective arcs, in unison, about subject 20.

Figure 12A:
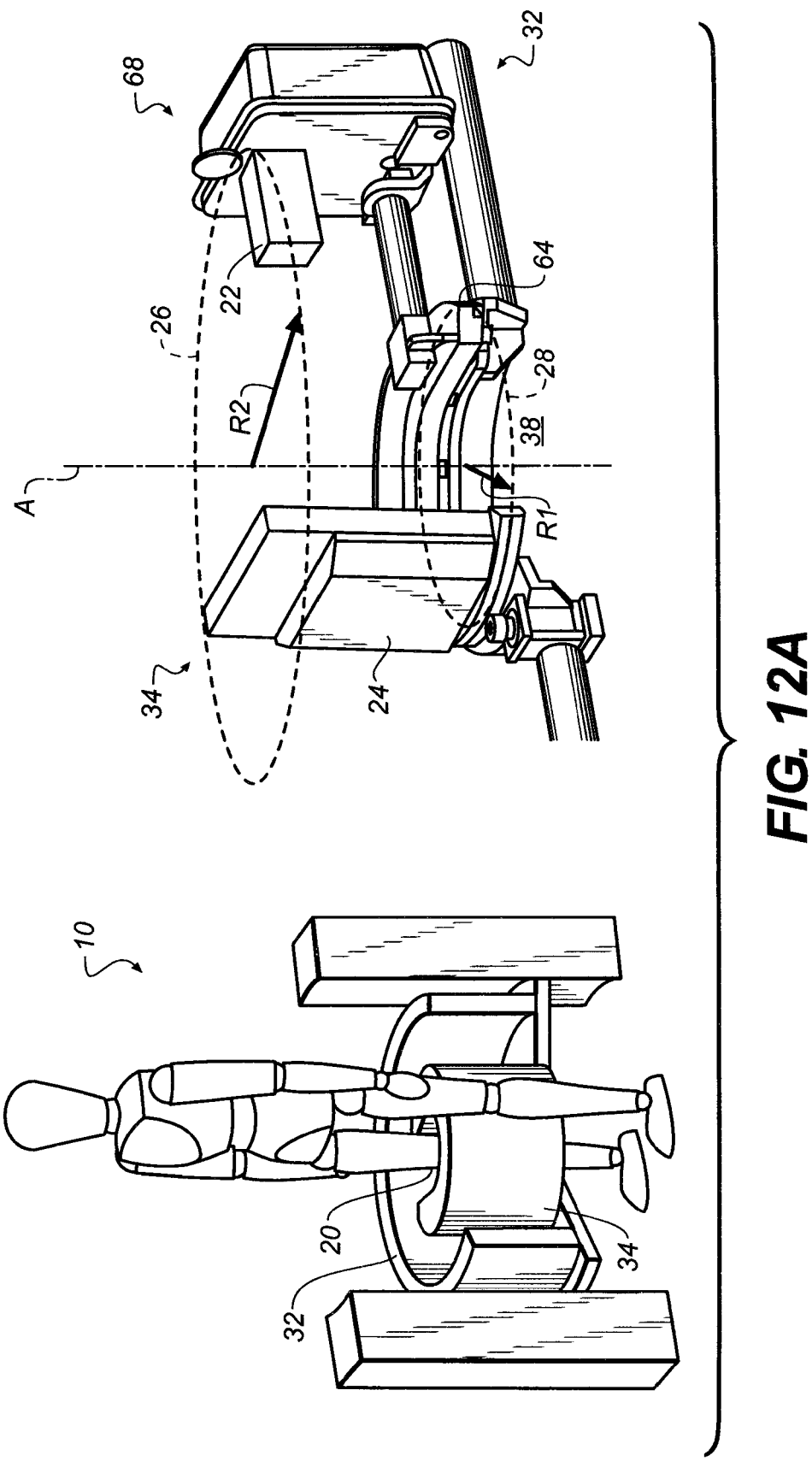
FIG. 12A shows perspective views of imaging apparatus with and without covers.

In an alternate embodiment, source and detector transport components are mechanically linked to a single revolving or rotating assembly. One such arrangement, shown at the right in FIG. 12A and enlarged in FIG. 12B, provides source and detector transports 32 and 34 using a single mechanical assembly, a rotating member 68, on a turntable 64 that revolves about central axis of rotation A and provides the needed radii for source 22 and detector 24. As is best shown in the top view of FIG. 13, detector 24 rides along the surface of the C-shaped turntable 64, orbiting the subject at radius R1. Source 22 is connected to turntable 64 along an arm 66 that provides the longer radius R2. Circumferential gap 38 extends across both source and detector paths.

It is noted that the embodiments shown using rotating member 68 on turntable 64 can be encased in one or more housings, thereby providing similar appearance to imaging apparatus 10 shown in FIGS. 7-11, for example. This type of arrangement has advantages for isolating the patient from moving components and for alleviating at least some of the patient anxiety that might be caused by automatically moving components during imaging.

Figure 14A:
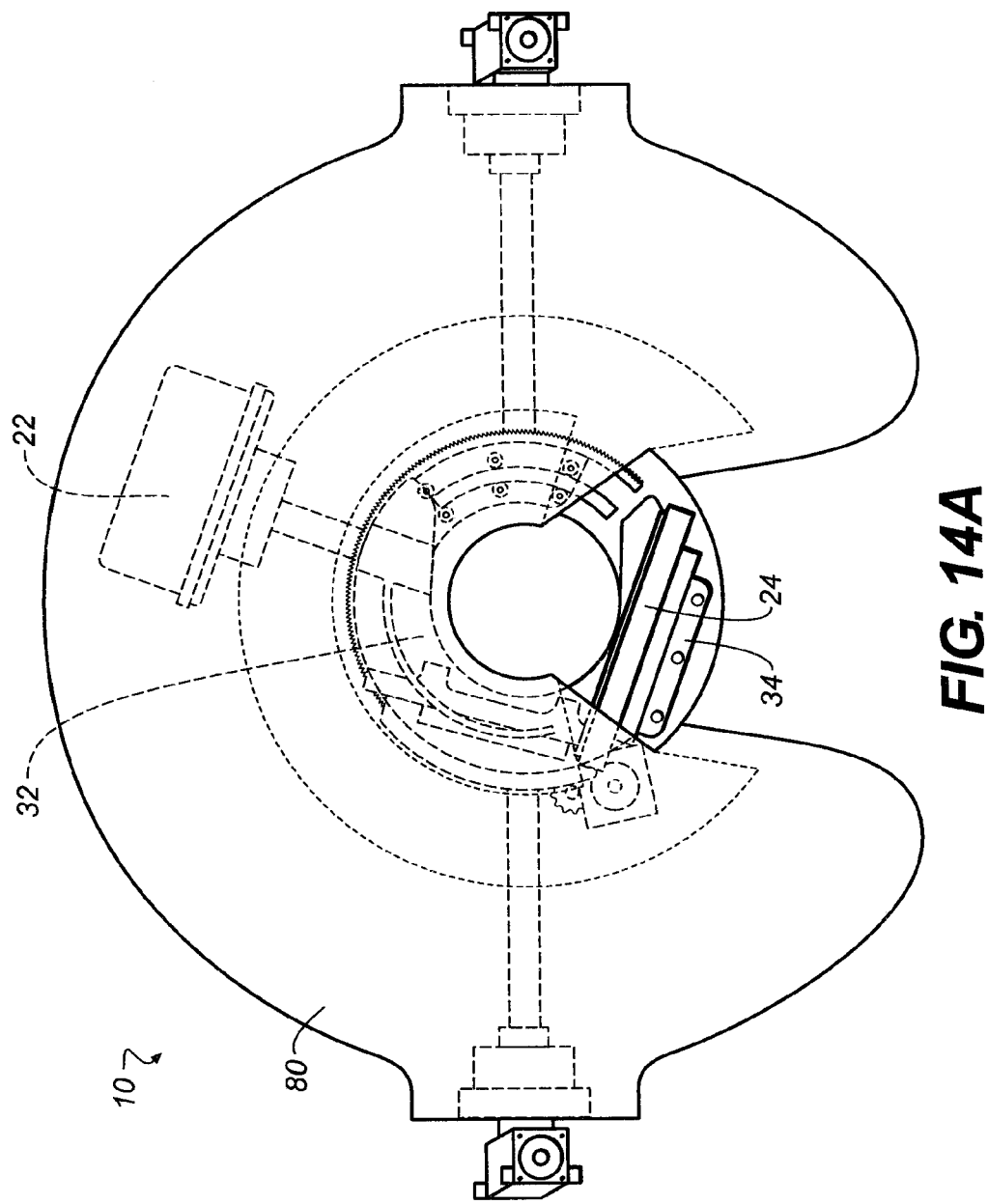
FIG. 14A shows a top view of the imaging apparatus with the housing partially transparent.
Figure 14B:
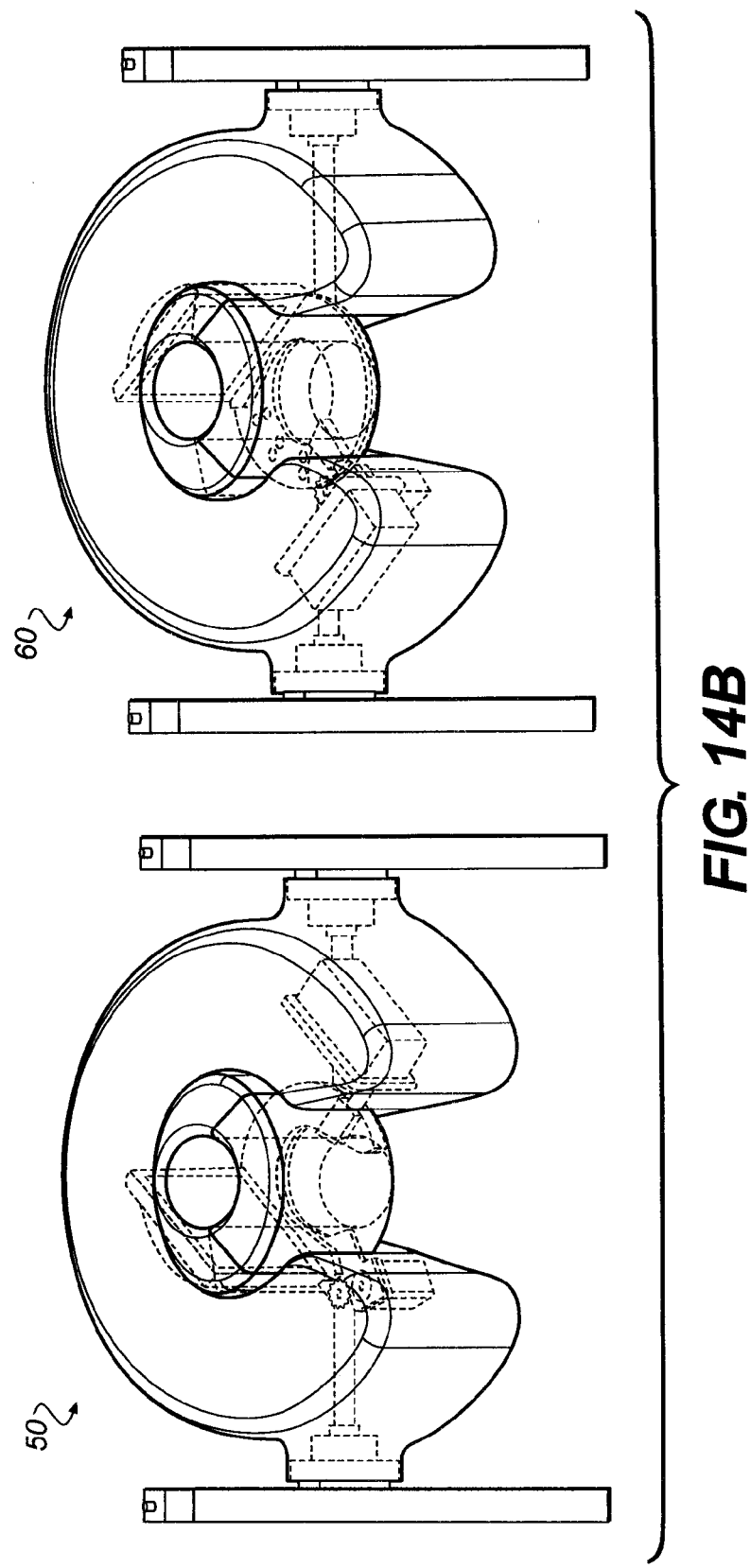
FIG. 14B shows internal components in start and stop scan positions.

FIG. 14A shows sources and detector transports 32 and 34 and source and detector 22 and 24 components as they are fitted within covers 80 that protect moving mechanical parts and help to prevent patient contact with moving components. FIG. 14B shows the covered system with internal components in begin and end scan positions 50 and 60 respectively, when using the scan sequence described earlier with reference to FIG. 6.

Figure 13:
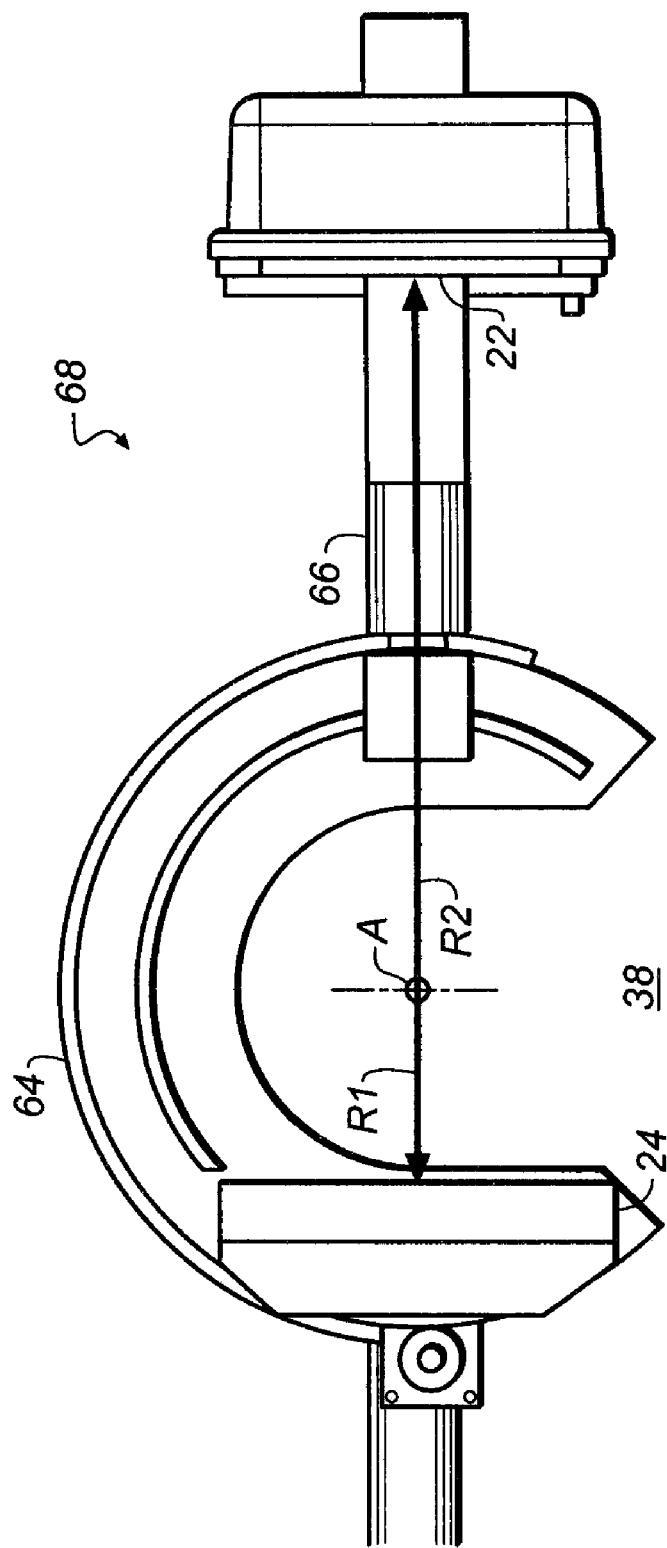
FIG. 13 is a top view of the transport arrangement shown in FIG. 12B.
Figure 15:
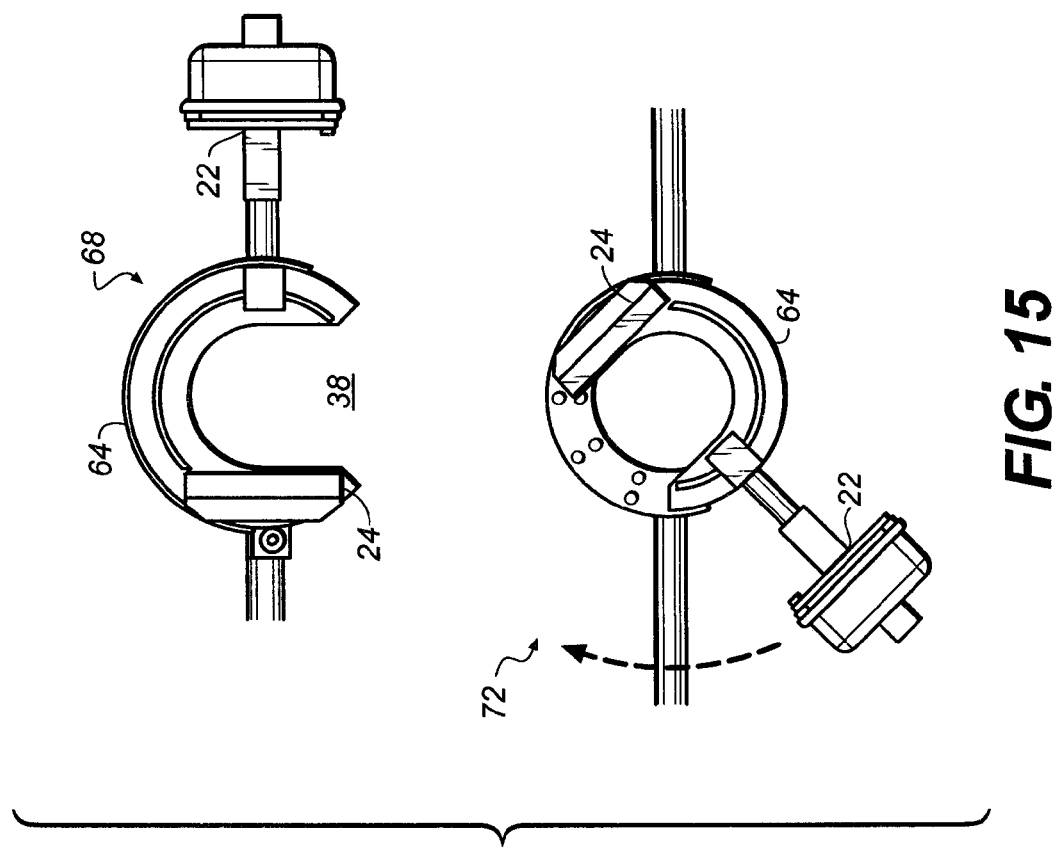
FIG. 15 shows top views of the turntable transport arrangement for initial positioning of the extremity of the patient and beginning of scan.
Figure 16:
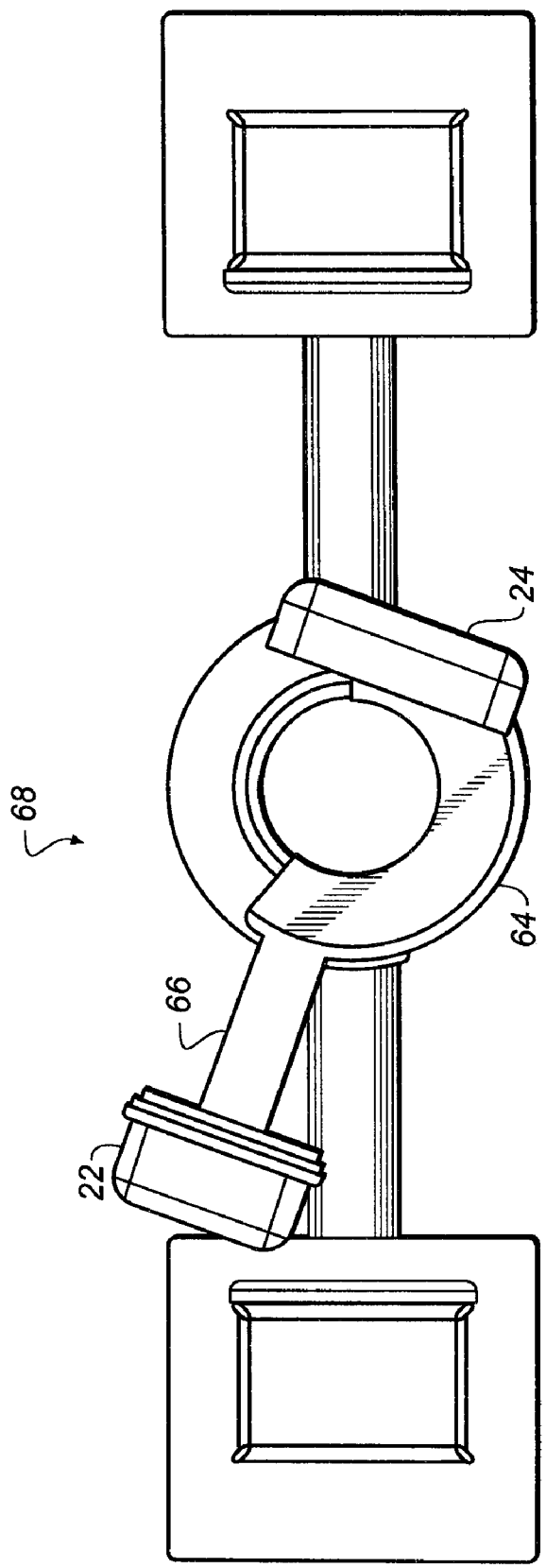
FIG. 16 shows a top view during the scan sequence.

The top views of FIGS. 13, 15, and 16 show how patient access is provided using this mechanical arrangement. Once the patient is positioned, rotating member 68 is swung around the positioned extremity, to a start position 72, as shown at the bottom in FIG. 15. Imaging begins at this position and continues as rotating member 68 revolves source and detector components about axis A. For the example of FIGS. 15 and 16, rotating member 68 moves in a clockwise direction. Counter-clockwise rotation would also be possible.

Figure 17:
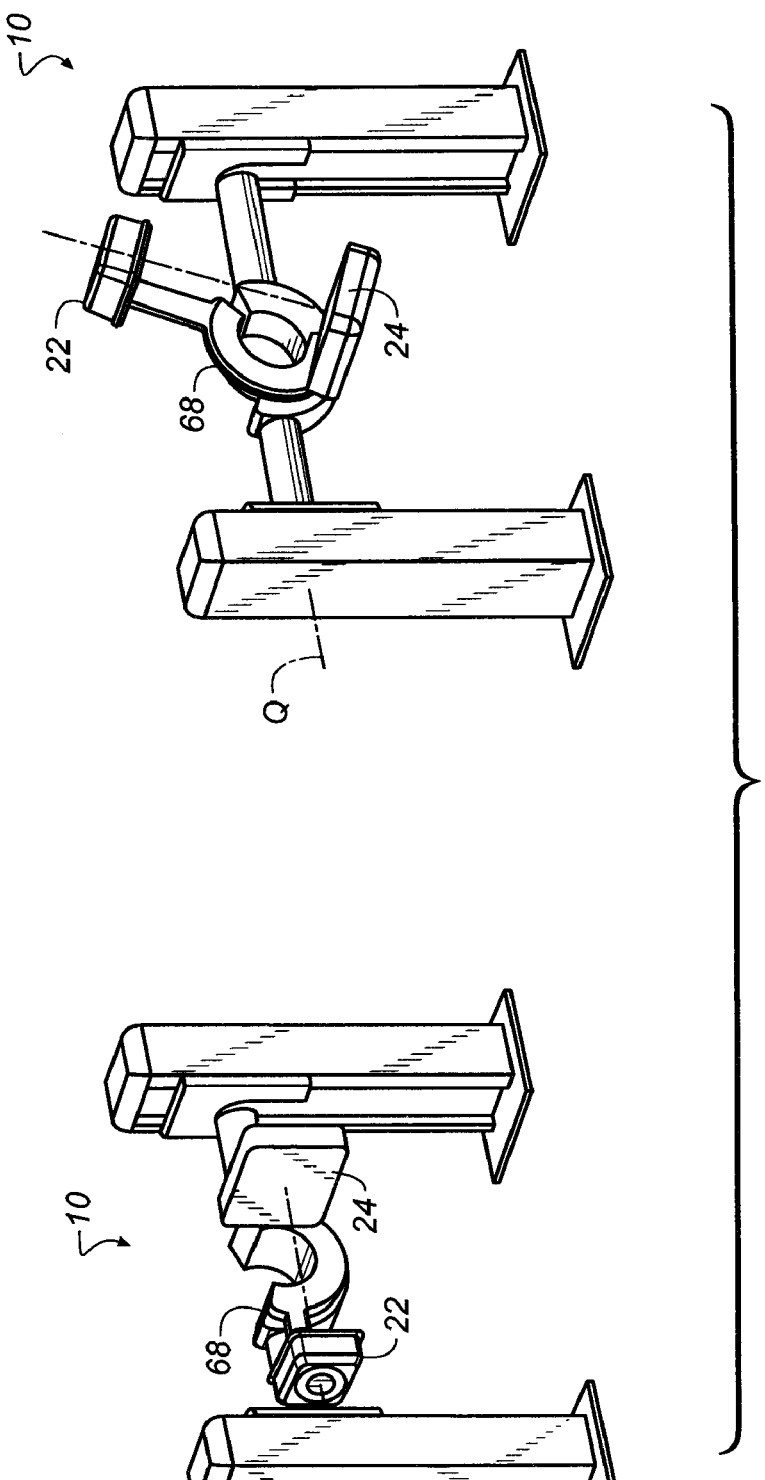
FIG. 17 shows perspective views of an embodiment for extremity imaging at a horizontal position.

Rotating member 68 can also be used with an imaging configuration for upper extremities, as shown in FIG. 17. Because none of the patient anatomy blocks the transport path, a full circular orbit is permitted for scanning with this configuration. Again, full 360 degree rotation of the components in the plane of rotating member 68 is possible, about tilt axis Q.

Figure 18A:
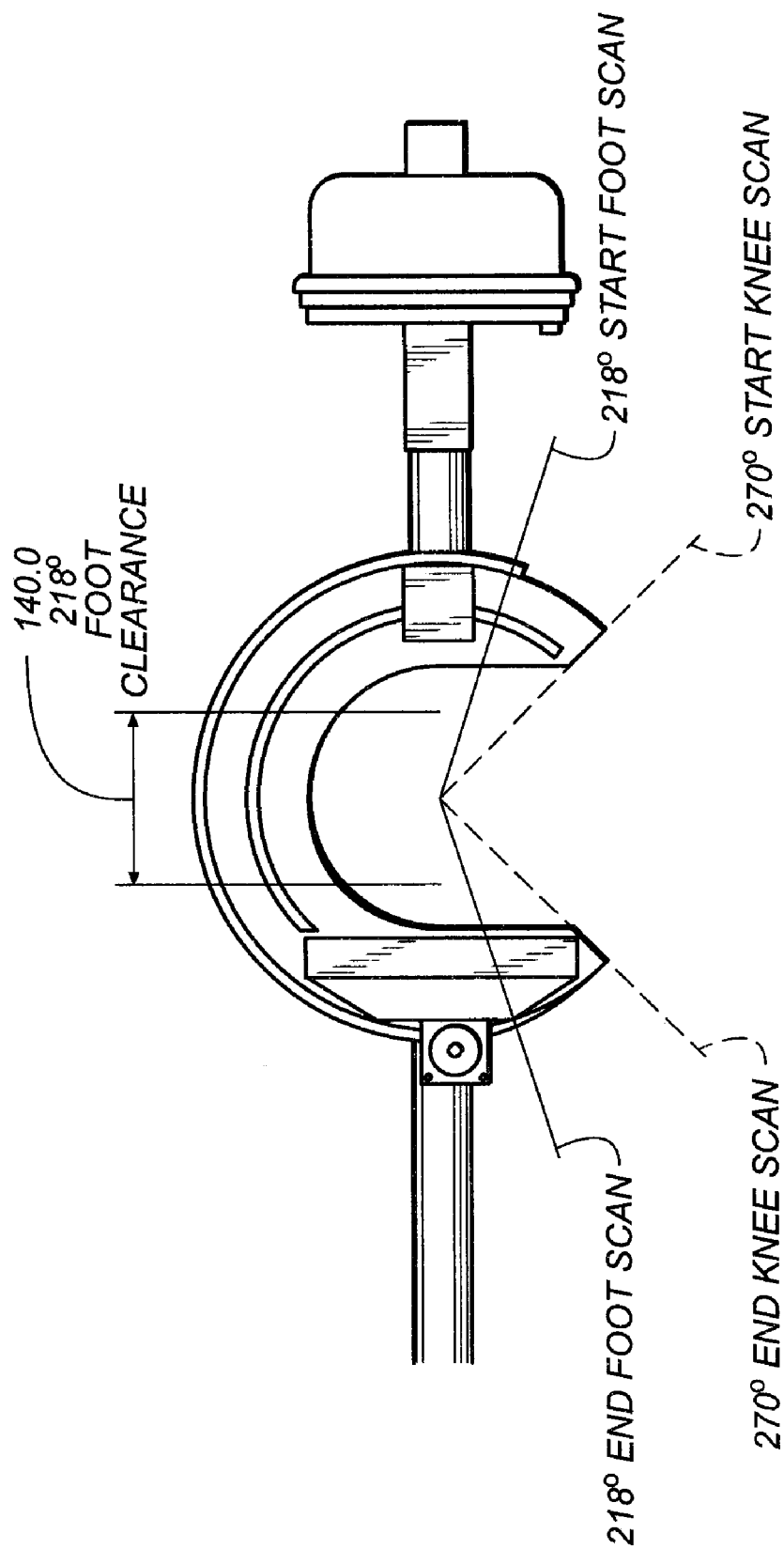
FIG. 18A is a top view that compares angular considerations for foot and knee imaging.

In the context of the present disclosure, the term "lower leg" is considered to include any portion of the human leg from just above the knee outward, thus including the knee as well as tibia/fibula structures, ankle, and foot. Imaging of extreme portions of the lower leg, including the ankle and foot is also possible with CBCT imaging apparatus 10. However, because the foot protrudes outward into the desired detector transport path, the allowable angular range for foot imaging is more constrained than the range for leg and knee imaging in general. The top view of FIG. 18A shows, for example, that the angular range for CBCT scanning of the foot, for a standing patient using CBCT imaging apparatus 10 described previously, is about 50 degrees less than that for knee imaging, for example.

As shown schematically in FIG. 18B, the general shape of the foot makes it difficult to image in a CBCT apparatus with the arrangement just described for CBCT imaging apparatus 10. In this figure, the inner dashed line circle represents the possible arcuate detector path 28; the outer dashed circle represents the possible arcuate source path 26. Paths 26 and 28 both lie in a transport plane T that can be tilted, as described subsequently. As shown previously, paths 26 and 28 are concentric and source and detector devices are arranged to be opposite each other along these respective paths. Where the foot is extended, source path 26 is not obstructed by patient anatomy. Because of limitations to detector path 28, which must be in the form of a circular arc that substantially extends from one side of the foot to the other, different approaches are needed for obtaining suitable projection images of the foot and ankle.

Schematic diagrams of FIGS. 19A, 19B, and 19C show patient positioning for obtaining images of the foot under various conditions and tilt angles when using a CBCT imaging apparatus that is configured according to embodiments of the present invention. FIG. 19A shows patient positioning for CBCT imaging of the foot in a non-load-bearing position. The patient places one foot into a CBCT imaging apparatus 100, such as onto a pedestal indent 102 formed into a housing 80 of CBCT imaging apparatus 100 or other suitable support that maintains the foot at the proper height for imaging. Source 22 and detector 24 then orbit the foot over a range of angles for obtaining the needed image projections. Here, transport plane T is substantially horizontal. It should be noted that tilt axis Q, shown in FIGS. 8A, 8B, and elsewhere, is substantially parallel to transport plane T, but may lie above or below plane T.

FIG. 19B shows patient positioning for CBCT imaging of the foot in a load-bearing position. With this arrangement, the patient is able to stand in a natural position and apply some weight to the foot during imaging. Here, transport plane T is also substantially horizontal.

FIG. 19C is a schematic view showing patient positioning for CBCT imaging of the foot in a non-load-bearing application with the patient seated and the leg extended. This position takes advantage of the rotatable housing of CBCT imaging apparatus 100. Here, transport plane T is substantially vertical, or at other suitable upright angle.

Figure 20:
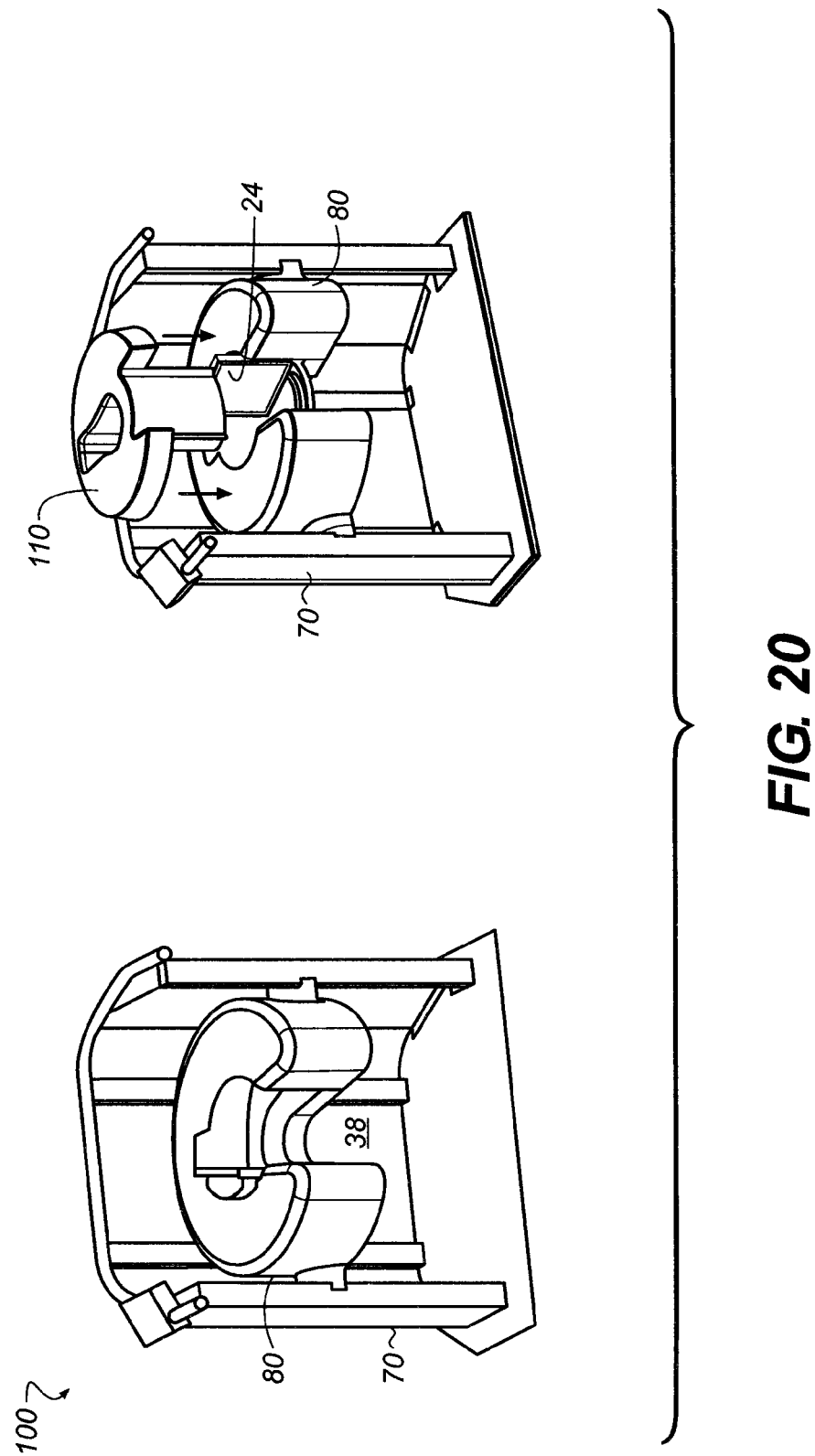
FIG. 20 shows perspective views of an imaging apparatus for foot imaging that employs an insert for setting up the detector path.

The perspective view of FIG. 20 shows an embodiment of CBCT imaging apparatus 100 that uses, as a type of detector path or gap closure apparatus, providing gap closure across circumferential gap 38 and enclosing the detector path, a removable insert 110 that is added to the base CBCT imaging apparatus when foot or ankle imaging is required. Insert 110 acts as a cover over the travel path of the detector and defines the boundaries of the detector orbit for foot imaging. Here, insert 110 slips into place within outer housing 80 as needed. Insert 110 is mechanically keyed to fit into housing 80 only in the proper orientation and is designed with interlocks that sense when insert 110 is in place and provide a signal to controlling logic to modify the source-detector paths accordingly. With insert 110 in place, closure of gap 38 is provided, completing the portion of the detector path that lies across gap 38.

Figure 21:
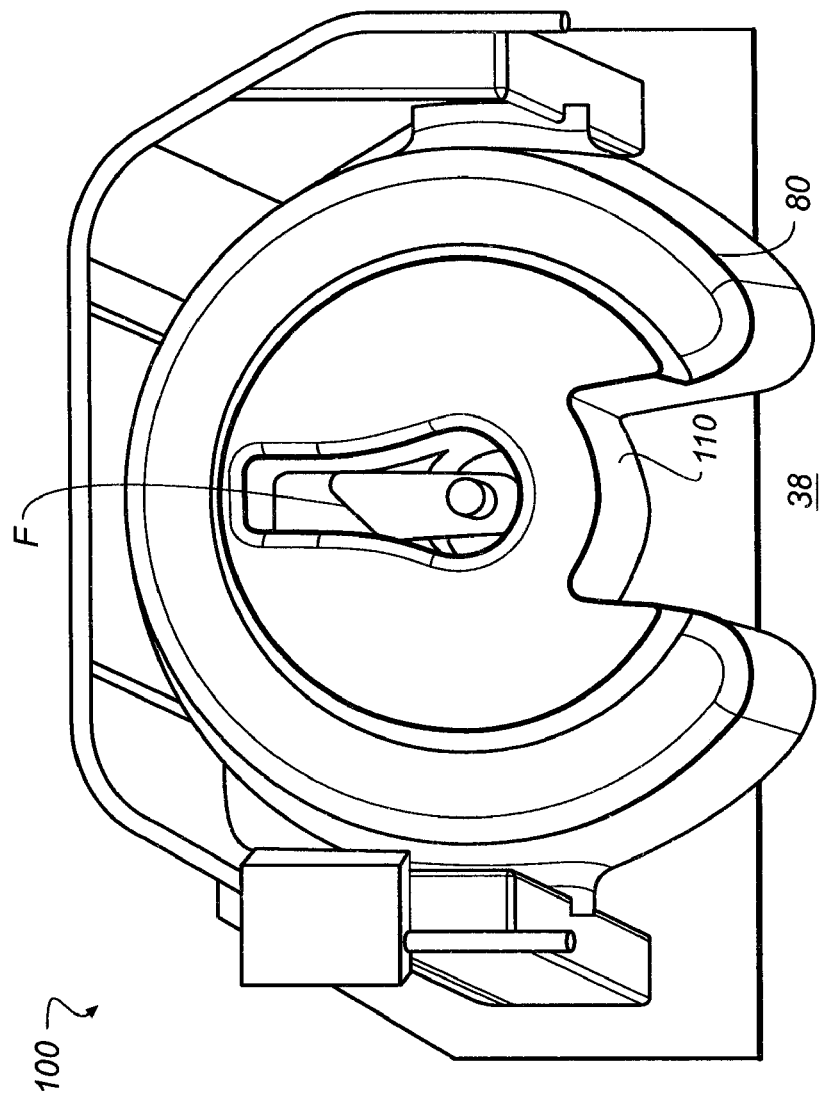
FIG. 21 is a top view of an imaging apparatus for foot imaging that employs an insert for setting up the detector path.
Figure 22:
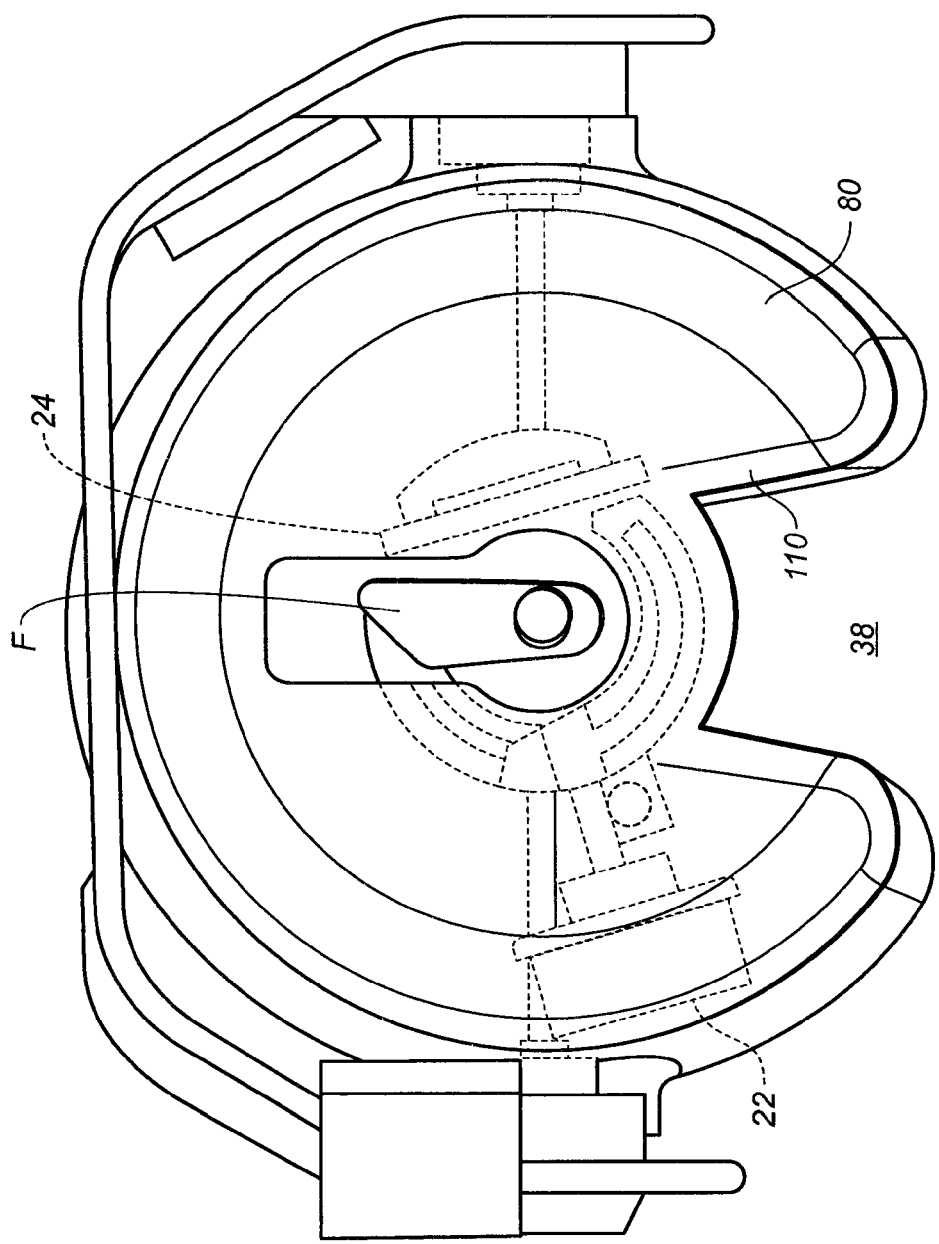
FIG. 22 is a top view of an imaging apparatus for foot imaging that employs an insert for setting up the detector path and with translucent covers.
Figure 23:
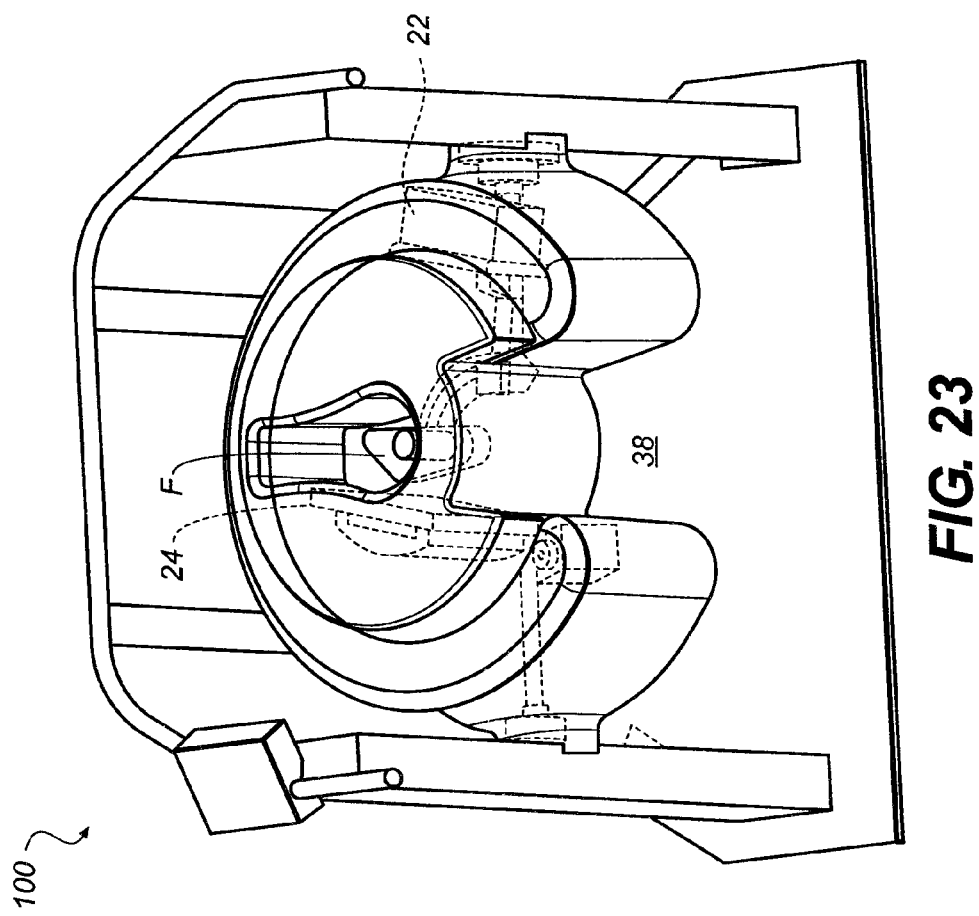
FIGS. 23, 24, and 25 are perspective views that show different positions of the imaging hardware for foot and ankle imaging.
Figure 24:
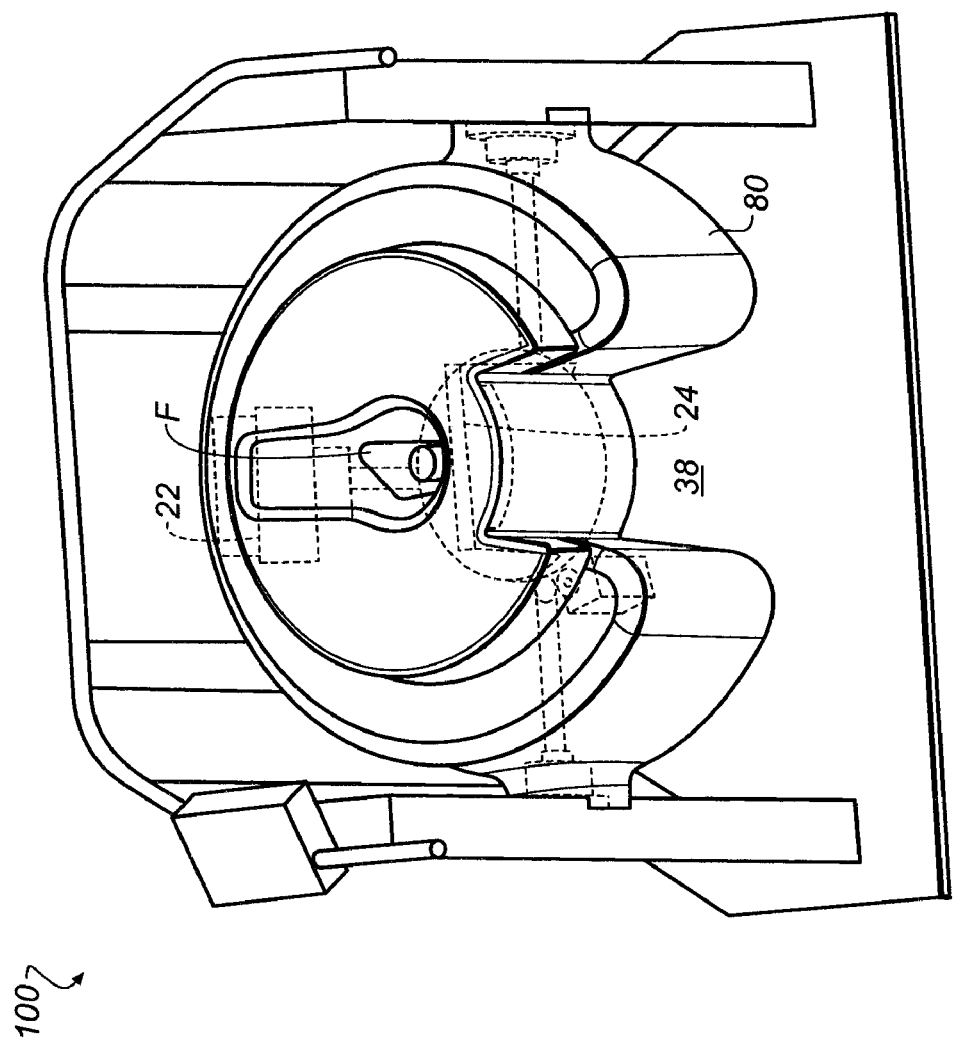
Figure 25:
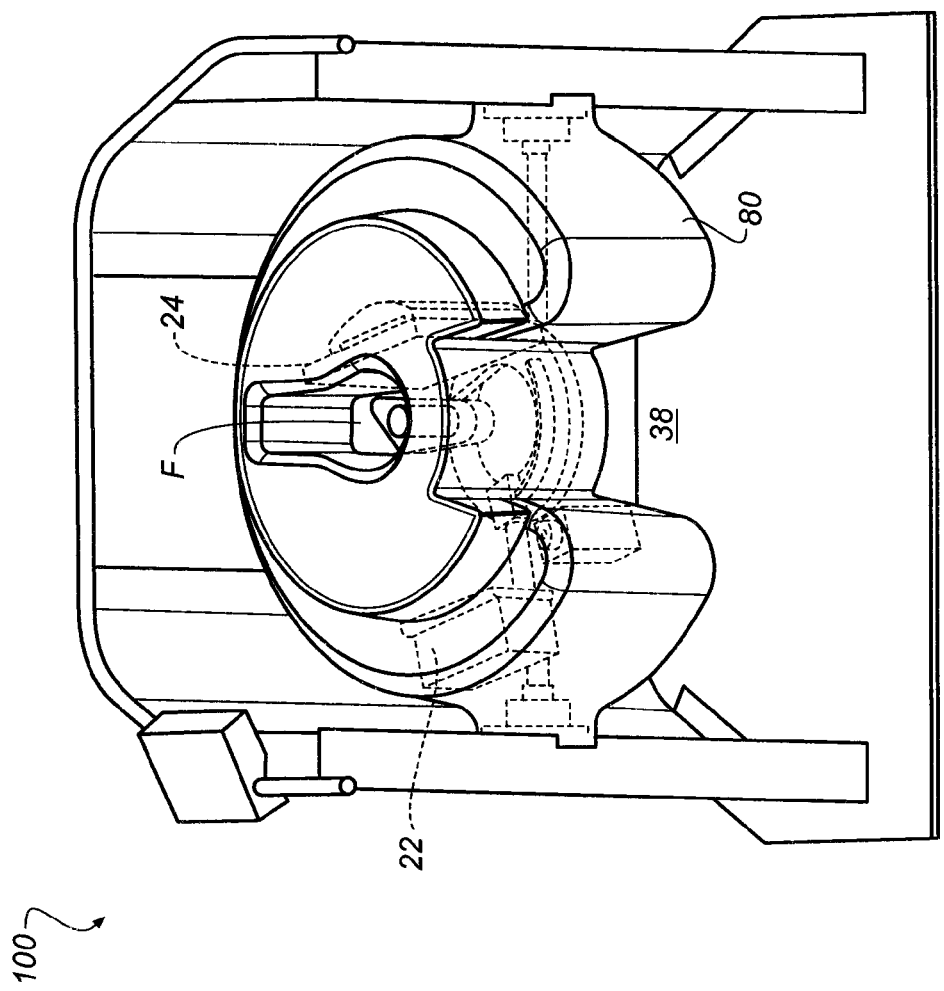

The top view of FIG. 21 shows from an outside view, with cover and housing opaque, insert 110 in place within CBCT imaging apparatus 100 and shows the reference position of a foot F when placed within insert 110. The top view of FIG. 22 shows the covers of insert 110 and housing 80 of imaging apparatus 100 as transparent, so that the positions of source 22 and detector 24 can be seen. For foot imaging, the travel path changes so that detector 24 travel is around the sides and rear of the foot and not around the front of the foot. This pattern is shown in the sequence of perspective views of FIGS. 23, 24, and 25. FIGS. 23 and 25 show the extreme ends of the detector 24 travel path. Where clockwise orbit is used, FIG. 23 shows the starting position of the detector 24 orbit and FIG. 25 the ending position. Where counter-clockwise movement is used, FIG. 25 shows the starting position for detector 24 and FIG. 23 the ending position.

Figure 26:
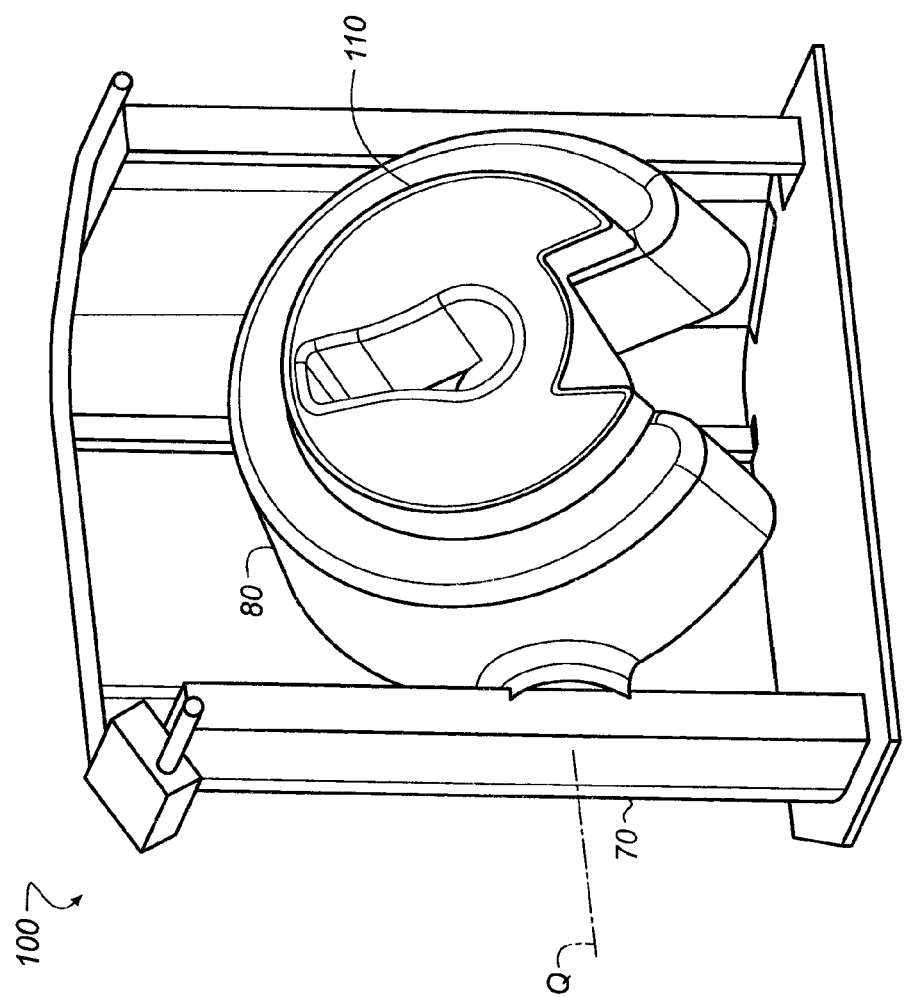
FIGS. 26 and 27 are perspective views showing a CBCT imaging apparatus rotated to different imaging positions.
Figure 27:
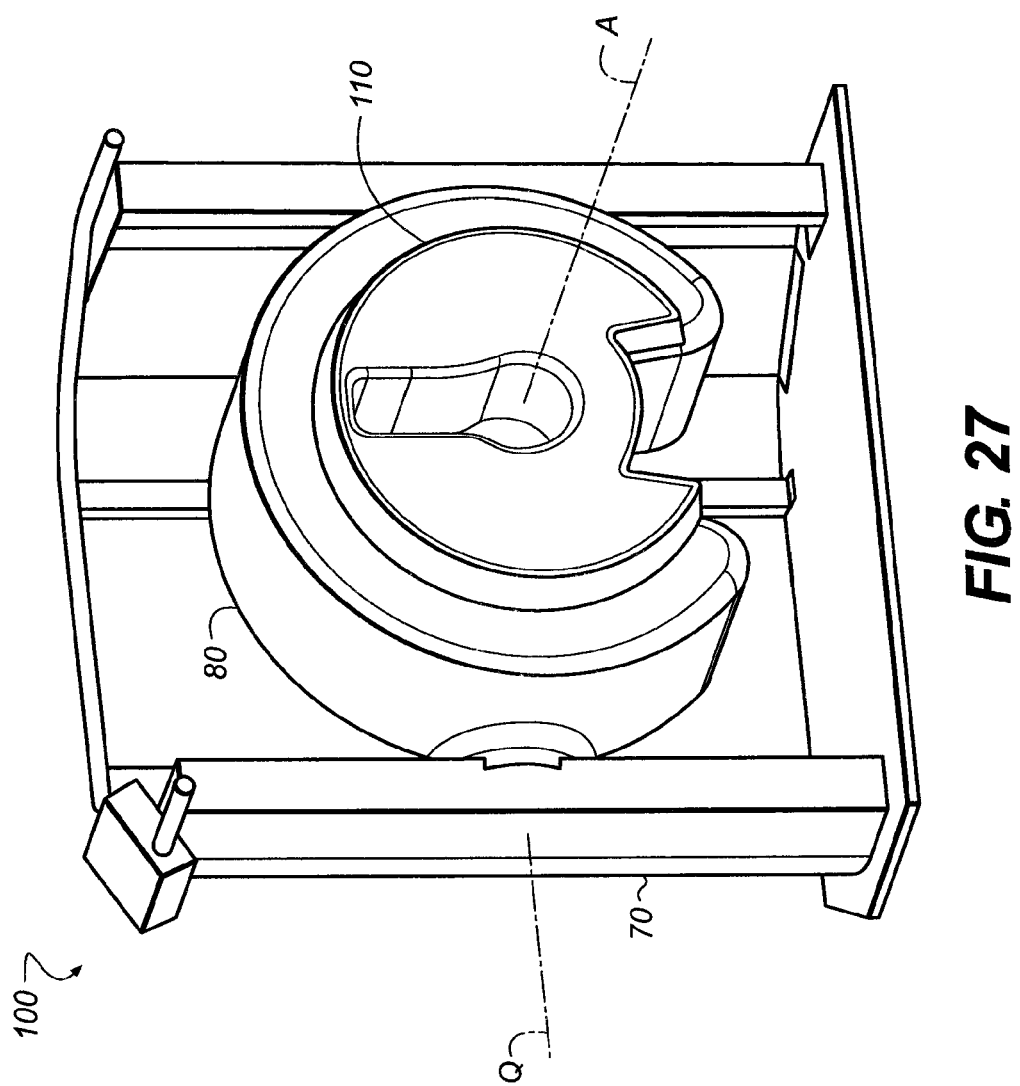

Height and angle adjustment are useful for foot and ankle imaging. FIGS. 26 and 27 show different rotation and height positions that can also be provided to allow more flexible patient positioning. For example, the arrangement shown in FIG. 27 is suitable for imaging of the foot with the patient in an extended leg position, as was described earlier with reference to FIG. 19C.

In addition to rotation about a tilt axis Q as shown in FIG. 27, housing 80 is also at least partially rotatable about a perpendicular vertical axis A, shown in FIG. 27 and elsewhere, in one embodiment.

Figure 28:
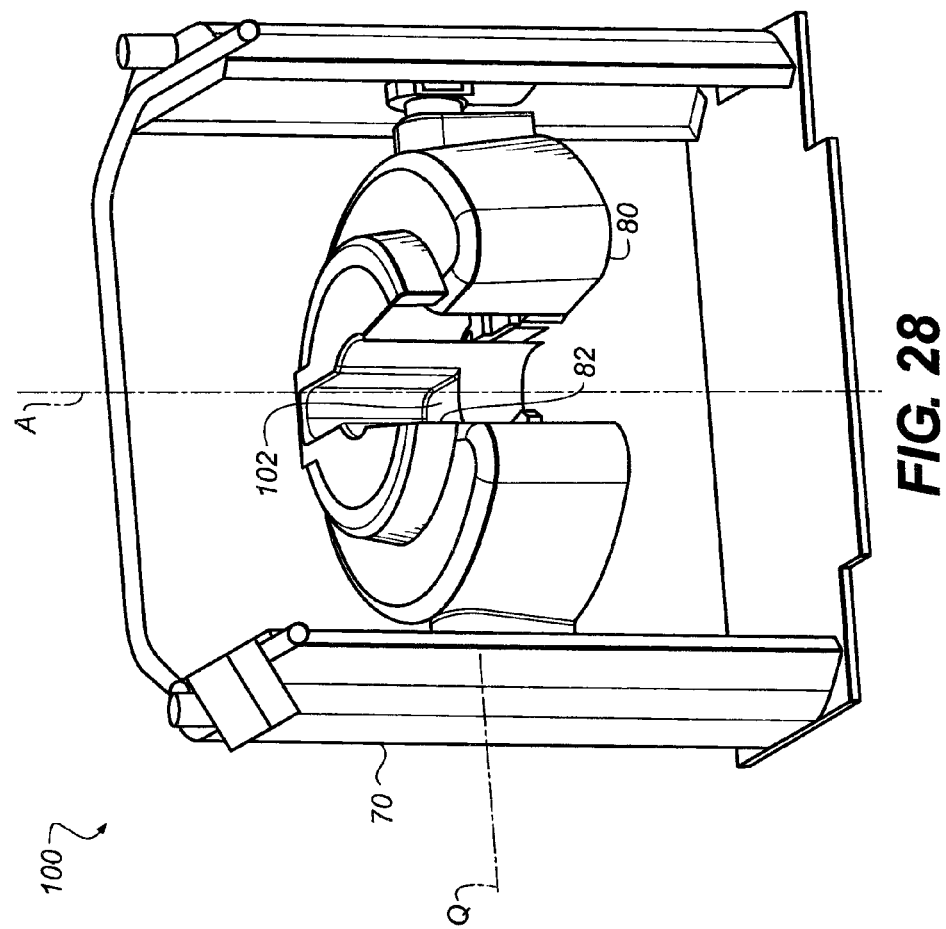
FIG. 28 is a perspective view of a CBCT imaging apparatus in an alternate embodiment that uses one or more doors to complete the detector path.
Figure 29:
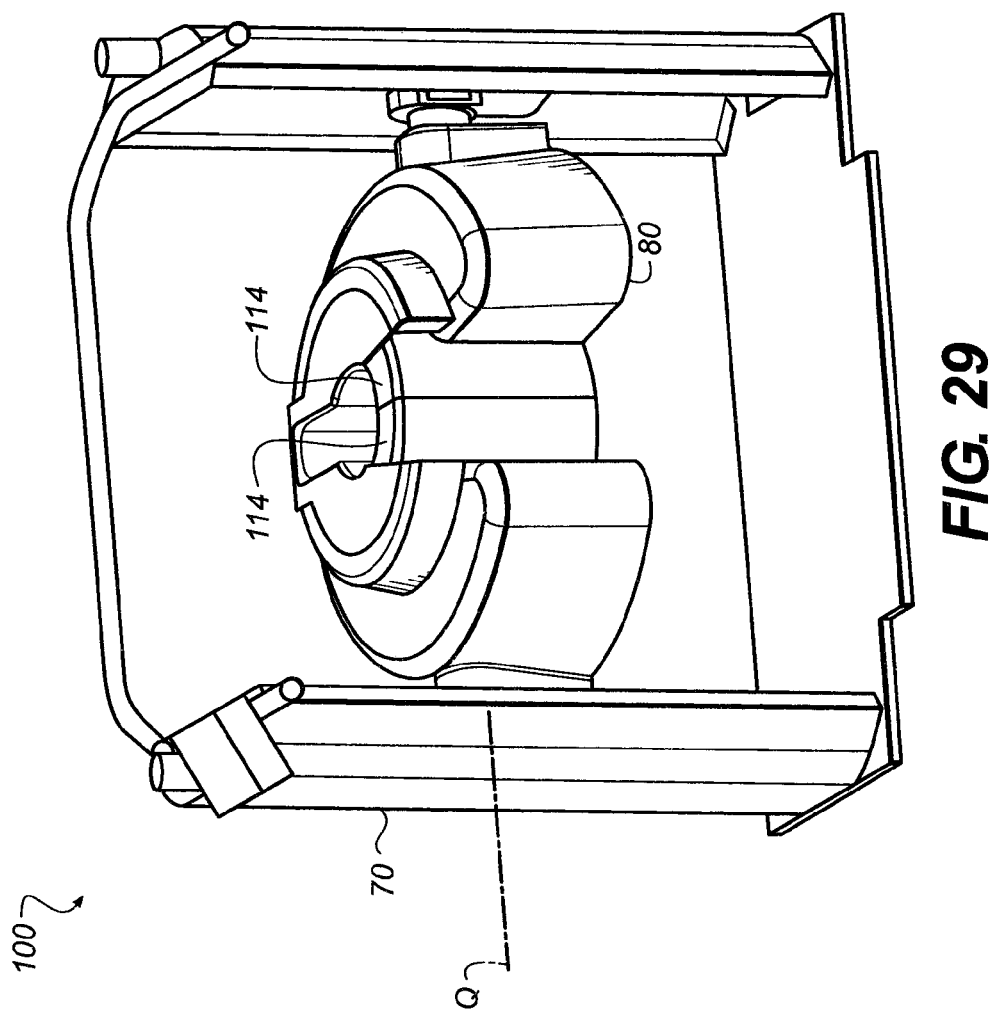
FIG. 29 is a perspective view of a CBCT imaging apparatus in the embodiment that uses one or more doors to complete the detector path, with the doors in closed position.
Figure 30:
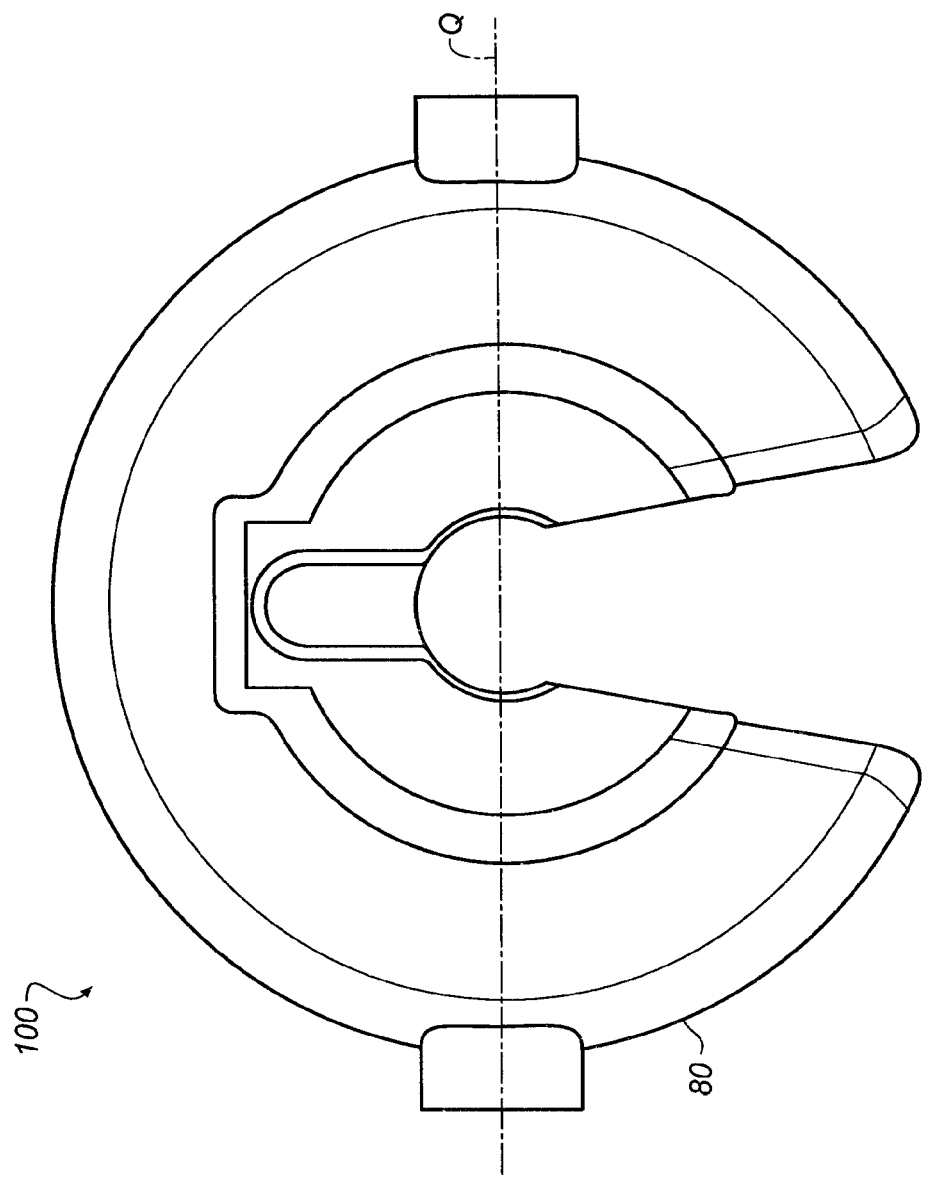
FIG. 30 is a top view of a CBCT imaging apparatus in an alternate embodiment that uses one or more doors to complete the detector path.
Figure 31:
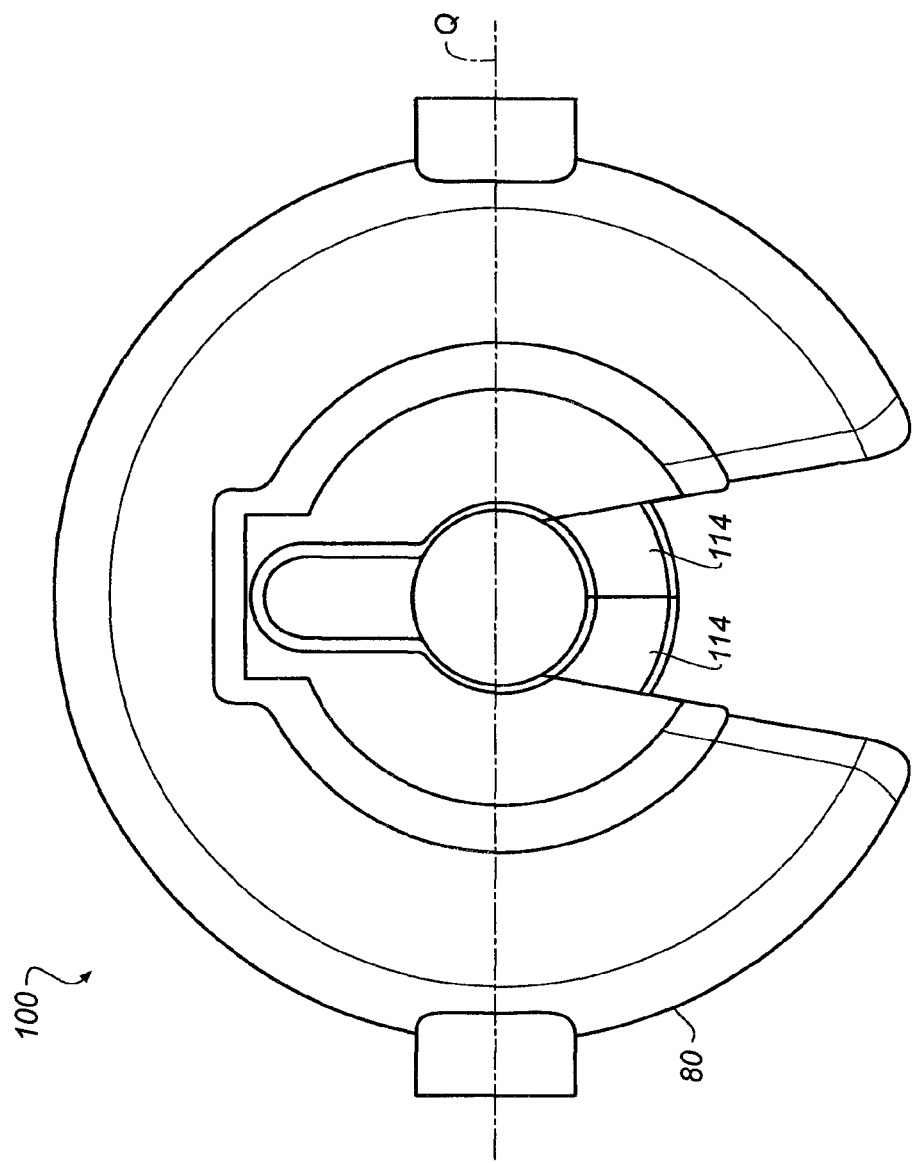
FIG. 31 is a top view of a CBCT imaging apparatus in the embodiment that uses one or more doors to complete the detector path, with the doors in closed position.

While insert 110 is useful as a detector path closure apparatus or gap closure apparatus for providing the continuation of the detector transport path around the back of the foot, the insert must be removed in order to allow imaging of the knee or other extremities. The alternate embodiment shown in FIGS. 28, 29, 30, 31, 32, and 33 uses an alternate approach to allow foot imaging or knee imaging using the same device. The perspective views of FIGS. 28 and 29 show CBCT imaging apparatus 100 that has a set of doors 114 that act as a gap closure apparatus for detector path closure and that enclose that portion of the arcuate detector path. Doors 114 are opened to allow entry of the patient's foot and can be closed once the foot is positioned on pedestal indent 102. Closing doors 114 completes detector path 28, extending this path behind the patient so that detector 24 can pass behind the foot during the CBCT image capture sequence, as was shown earlier with reference to FIGS. 23, 24, and 25. FIGS. 30 and 31 show door-open and door-closed positions from a top view for this alternate embodiment.

Figure 32:
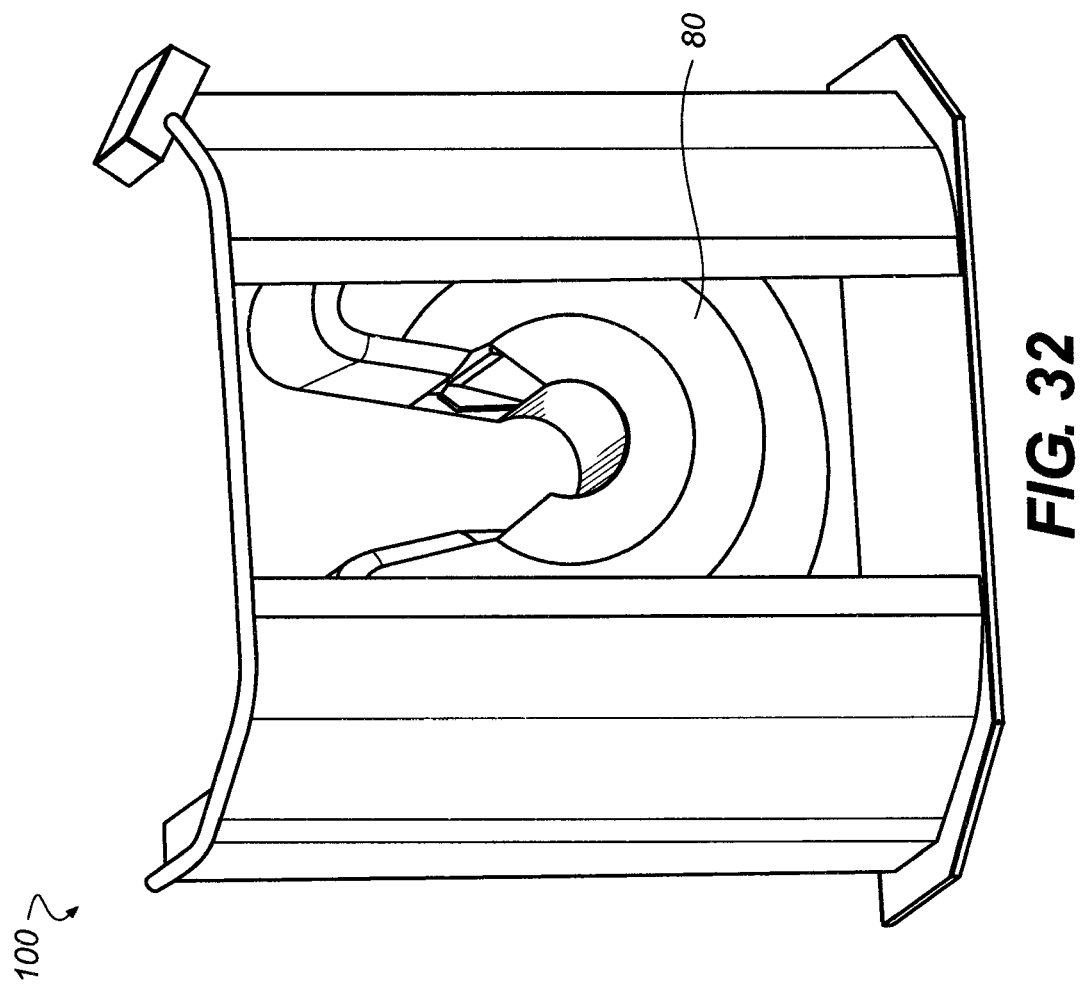
FIGS. 32 and 33 show door open and door closed positions, respectively, for a CBCT imaging apparatus in rotated position for extended leg imaging of the foot or ankle.
Figure 33:
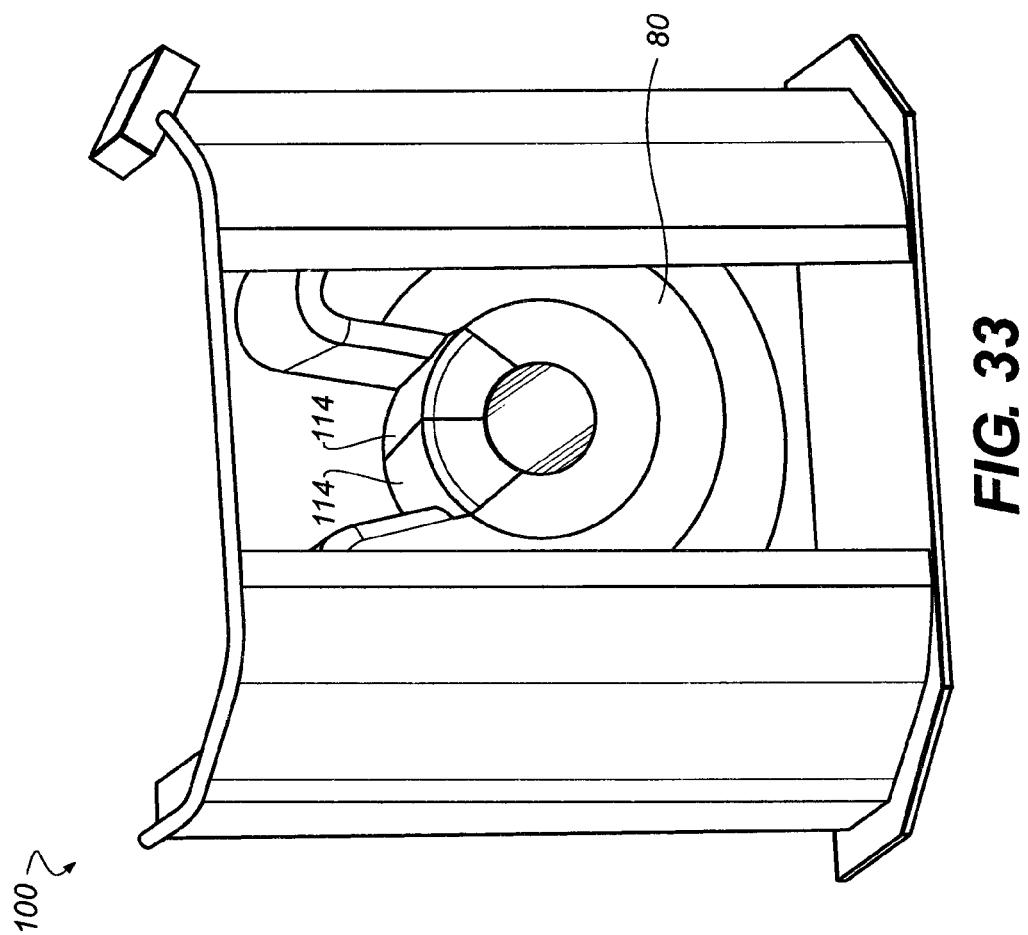

FIGS. 32 and 33 show door open and closed positions, respectively, with CBCT imaging apparatus 100 in rotated position for extended leg imaging of the foot or ankle. It should be noted that a single door could be used as an alternative to the double-door arrangement of FIGS. 28-33. A sensor 82 (FIG. 28) detects when a foot is positioned in the pedestal and adjusts the imaging and transport patterns accordingly.

The source-detector travel paths provided for the conventional patient positions shown in FIGS. 19A, 19B, and 19C can be used for accurate 3-D reconstruction of the ankle and upper areas of the foot, but can be of less accuracy for reconstructing a 3-D image of the foot itself. Referring to the schematic diagram of FIG. 34, it can be seen that the direct head-on radiation path P1 from source 22 to detector 24 is through a number of bone structures. This is a problem encountered by a scanning pattern in which the source and detector orbits are in the plane of radiation path P1. 3-D reconstruction from such an image is complicated by the presence of these bones in different arrangements for or missing from different image projections. One solution is to tilt the foot; however, this may not be possible for the patient. Moreover, having the patient hold the foot in an awkward position may not provide what is most helpful for diagnostic analysis. The pedestal (not shown for clarity in FIG. 34) seats the foot along a plane W that may or may not be horizontal.

An alternative solution that is available with embodiments of CBCT imaging apparatus 100 is to tilt the imaging apparatus itself about tilt axis Q (FIG. 28 and elsewhere), at an angle θ so that housing 80 is at an oblique angle by 1 or more degrees relative to either the horizontal or vertical, such as at 10, 20, or 40 degrees.

Figure 34:
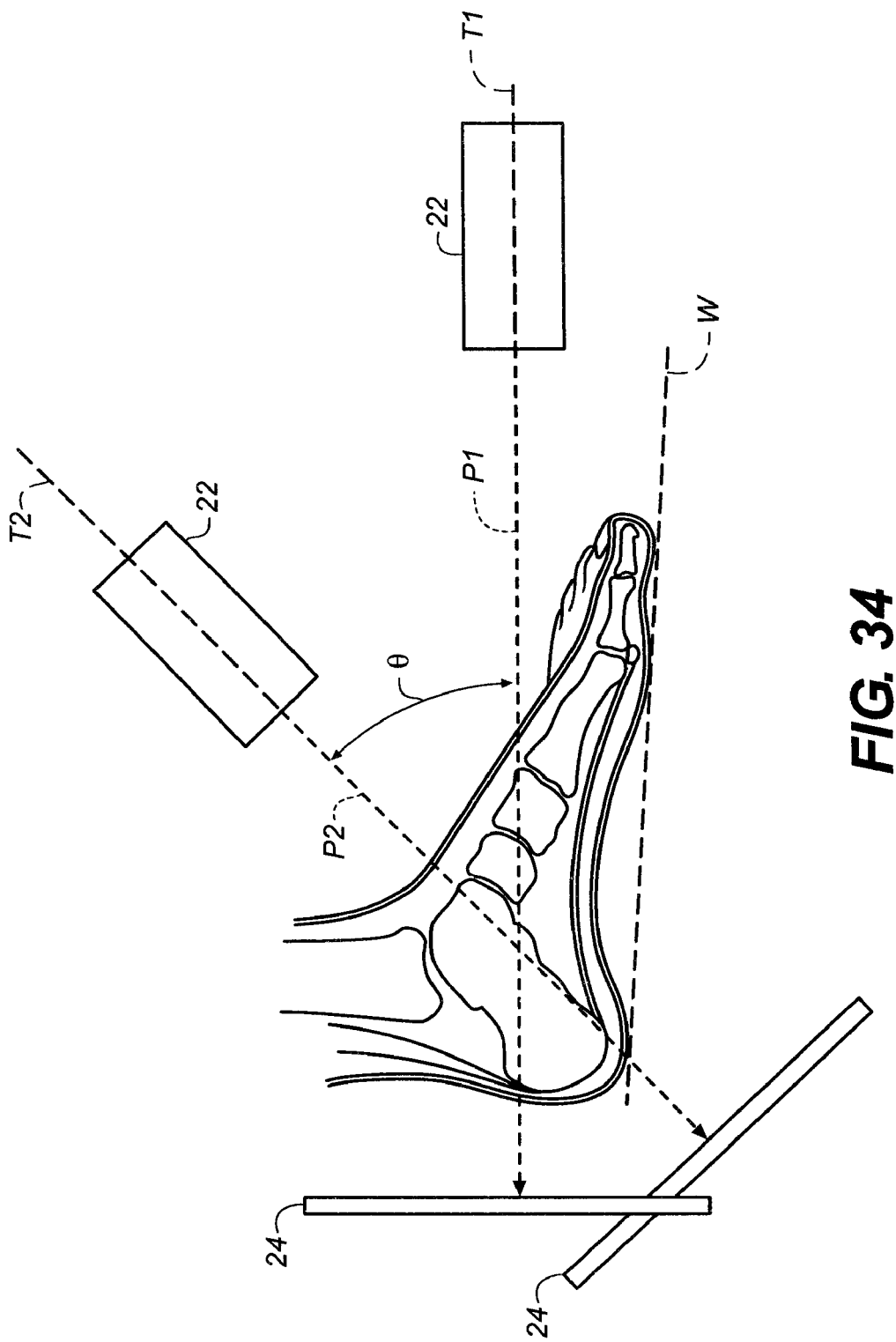
FIG. 34 is a schematic diagram showing alternate radiation paths for foot and ankle imaging.

With respect to the schematic diagram in FIG. 34, this arrangement allows the source and detector orbits in transport plane T to be shifted to any of a range of angular positions, shown as planes T1 and T2 corresponding to paths P1 and P2, for example, allowing improved imaging of parts of the foot and ankle. As is shown in FIG. 34, this arrangement effectively tilts transport plane T to any of a range of angles relative to plane W of the foot, so that planes W and T are at different angles. The tilt angle of the tilt axis can thus be disposed to direct radiation to the foot at an angle that is offset from base of the foot by a variable range, from a few degrees to more than 10 or 20 degrees, and even allowing the tilt axis to vary over a full 90 degree range or more for this purpose.

Figure 35B:
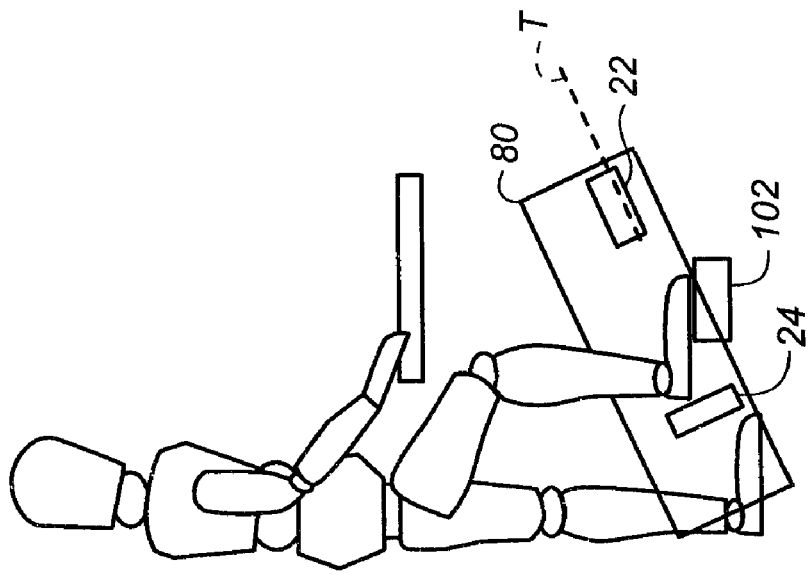
FIG. 35B is a schematic diagram that shows a housing inverted and tilted to an oblique angle for foot imaging according to an alternate embodiment.
Figure 35A:
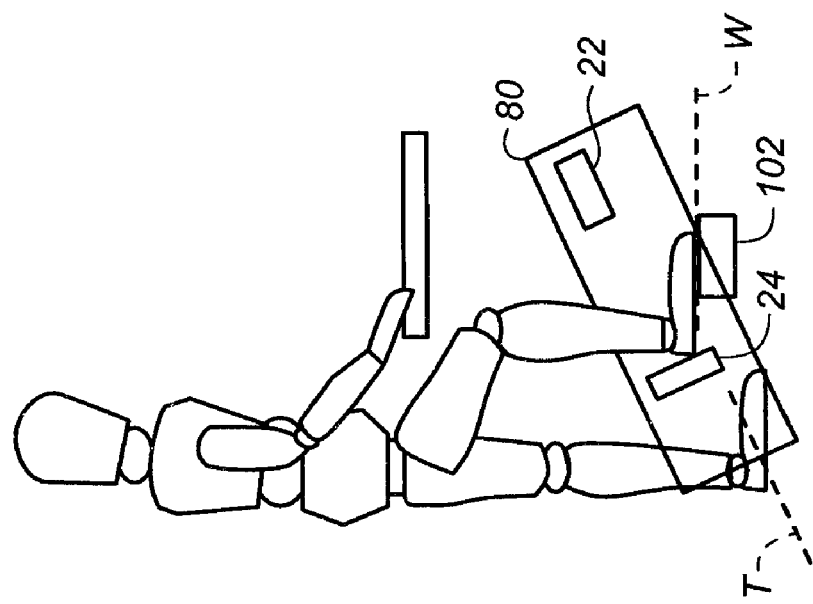
FIG. 35A is a schematic diagram that shows a housing tilted to an oblique angle for foot imaging according to one embodiment of the present invention.

The schematic diagram of FIG. 35A shows housing 80 tilted to an oblique angle for foot imaging according to one embodiment. This orients the orbits of source 22 and detector 24 to an oblique angle with respect to horizontal and also expands the possible angular range of both source and detector travel paths. The schematic diagram of FIG. 35B shows an alternate arrangement, with housing 80 inverted and at an oblique angle, for improving the image coverage of parts of the foot.

Figure 36B:
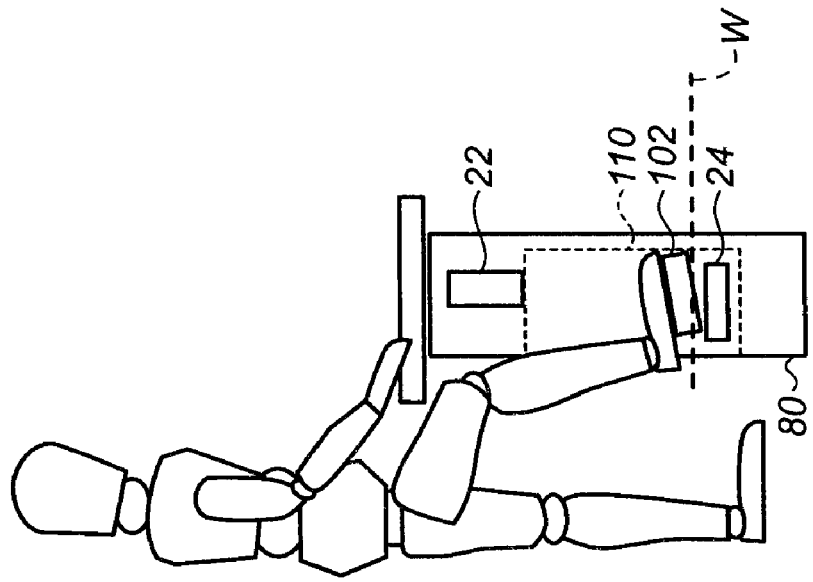
FIG. 36B is a schematic diagram that shows a housing with a foot insert tilted to an angle for foot and toe imaging according to an alternate embodiment.
Figure 36A:
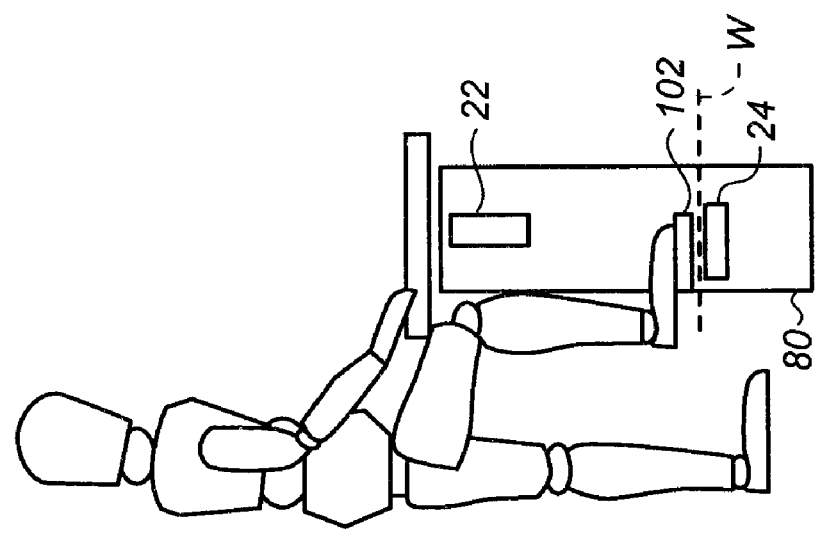
FIG. 36A is a schematic diagram that shows a housing without a foot insert tilted to an angle for foot and toe imaging according to an alternate embodiment of the present invention.

Because such an extended angular range is permitted, the problem of imaging for the front of the foot and imaging of the toes can also be addressed by embodiments of the present invention. FIG. 36A shows an embodiment without using foot insert 110. In this embodiment, the extended foot can be positioned for imaging, but the shin of the leg prevents the foot from being fully extended into the imaging area. With foot insert 110, as shown in FIG. 36B, the foot can be extended a few more inches into the imaging area, since the shin of the patient has more room to be moved forward.

It can be appreciated that the alternate embodiment shown in FIGS. 28-33, not using insert 110 but instead using some sort of sliding door arrangement, has advantages over embodiments that require the use of insert 110. One advantage relates to more general use of CBCT imaging apparatus 100 for obtaining images of different extremities. For example, the same apparatus can be used for imaging a foot or ankle as well as for imaging a knee or other portion of the leg or other extremity.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for cone beam computed tomography of a portion of a lower leg of a patient, comprising:
    a source transport actuable to move a radiation source along at least a portion of an arcuate source path within a housing, wherein the source path extends from one side of a circumferential gap in the housing to the other side of the circumferential gap and has a radius R2 about a center;
    a pedestal indent on the housing for placement of the patient's foot;
    a digital radiation detector;
    a detector transport actuable to move the detector along at least a portion of an arcuate detector path within the housing, the detector path having a radius R1 about the center and concentric with the source path, wherein R1 is less than R2, and wherein the detector path extends from one side of the pedestal indent to the other; and
    a gap closure apparatus that is movable to a position that continues the detector path across the circumferential gap and that encloses the detector path across the gap.

2. The apparatus according to claim 1 wherein the gap closure apparatus comprises an insert fitted into the housing.

3. The apparatus according to claim 1 wherein the gap closure apparatus comprises one or more sliding doors in the housing.

4. The apparatus according to claim 1 wherein the housing is rotatable about an axis extending through the center of the arcuate source path.

5. The apparatus according to claim 1 further comprising a sensor that detects when a foot is positioned in the pedestal indent.

6. The apparatus according to claim 4 wherein the housing is further rotatable about an axis that extends through the housing, from one side of the housing to the other.

7. The apparatus according to claim 1 further comprising a vertical support for the housing and wherein the height of the housing is adjustable within the vertical support.

8. The apparatus according to claim 2 further comprising an interlock that provides a signal when the insert is in position in the housing.

9. A method for providing cone beam computed tomography of a foot of a patient, comprising:
mounting a radiation source on a source transport that is actuable to move the radiation source along at least a portion of an arcuate source path within a housing, wherein the source path extends from one side of a circumferential gap in the housing to the other side of the circumferential gap and has a radius R2 about a center and wherein the source path defines a transport plane;
providing a pedestal for placement of the patient's foot to receive radiation from the radiation source;
mounting a digital radiation detector on a detector transport that is actuable to move the digital radiation detector along at least a portion of an arcuate detector path within the housing, the detector path having a radius R1 about the center and concentric with the source path, wherein R1 is less than R2, and wherein the detector path extends from one side of the pedestal to the other and lies within the transport plane; and
providing a gap closure apparatus that is movable to a position that extends the detector path across the circumferential gap.

10. The method of claim 9 further comprising mounting the housing to a support that provides a tilt axis for tilting the transport plane to any of a plurality of tilt angles over a range of tilt angles, wherein the tilt axis is substantially parallel to the transport plane.

11. The method of claim 10 wherein the pedestal seats the foot at a first angle and the tilt angle is adjustable to a range of different angles relative to the first angle.

12. The method of claim 11 wherein the tilt angle of the tilt axis is disposed to direct radiation to the foot at an angle that is offset from the first angle by more than 2 degrees.

13. The method of claim 9 wherein the gap closure apparatus comprises a removable insert to the housing.

14. The method of claim 9 wherein positioning the gap closure apparatus comprises rotating into position one or more doors from within the housing that covers the radiation source and detector.

15. The method of claim 9 wherein the pedestal is formed into the housing.

* * * * *